United States Patent
Choi et al.

(10) Patent No.: US 10,262,175 B2
(45) Date of Patent: Apr. 16, 2019

(54) WRAPPER FOR TERAHERTZ, DETECTION SENSOR, DETECTION APPARATUS USING TERAHERTZ WAVE, OPTICAL IDENTIFICATION DEVICE FOR TERAHERTZ, APPARATUS FOR RECOGNIZING OPTICAL IDENTIFICATION DEVICE FOR TERAHERTZ WAVE, AND WRITING APPARATUS FOR IDENTIFICATION UNIT

(71) Applicant: KOREA FOOD RESEARCH INSTITUTE, Seongnam-si, Gyeonggi-do (KR)

(72) Inventors: Sung Wook Choi, Yongin-Si (KR); Hyun Jung Kim, Seoul (KR); Na Ri Lee, Seoul (KR); Hyun Joo Chang, Seoul (KR); Gyeong Sik Ok, Osan-si (KR)

(73) Assignee: KOREA FOOD RESEARCH INSTITUTE, Seongnam-si (KR)

( * ) Notice: Subject to any disclaimer, the term of this patent is extended or adjusted under 35 U.S.C. 154(b) by 25 days.

(21) Appl. No.: 15/065,798

(22) Filed: Mar. 9, 2016

(65) Prior Publication Data
US 2016/0259959 A1 Sep. 8, 2016

Related U.S. Application Data

(63) Continuation of application No. 14/905,962, filed as application No. PCT/KR2013/010008 on Nov. 6, 2013.

(30) Foreign Application Priority Data

Jul. 19, 2013 (KR) .................. 10-2013-0085144
Aug. 21, 2013 (KR) .................. 10-2013-0099112

(51) Int. Cl.
*B32B 3/26* (2006.01)
*B32B 15/04* (2006.01)
(Continued)

(52) U.S. Cl.
CPC .............. *G06K 7/1413* (2013.01); *B32B 3/06* (2013.01); *B32B 3/266* (2013.01); *B32B 7/12* (2013.01);
(Continued)

(58) Field of Classification Search
CPC ............................................. G01N 2021/7769
See application file for complete search history.

(56) References Cited

U.S. PATENT DOCUMENTS

| | | |
|---|---|---|
| 2009/0314944 A1 | 12/2009 | Evans et al. |
| 2010/0148050 A1* | 6/2010 | Bari ................ B82Y 20/00 |
| | | 250/271 |

FOREIGN PATENT DOCUMENTS

| | | |
|---|---|---|
| EP | 2199799 A1 | 6/2010 |
| KR | 10-2011-0009887 A | 1/2011 |

(Continued)

OTHER PUBLICATIONS

International Search Report dated Apr. 12, 2014 in PCT/KR2013/010008 4 pgs.

*Primary Examiner* — Edwin C Gunberg
(74) *Attorney, Agent, or Firm* — Ichthus International Law PLLC

(57) ABSTRACT

A wrapper for a terahertz wave according to an embodiment of the present invention includes: a terahertz wave transmission layer that is made of a material that transmits a terahertz wave; and an electric field enhancement structure that enhances an electric field by reacting with a predetermined frequency band of terahertz waves passing through the terahertz wave transmission layer. An optical identifica- (Continued)

tion device for a terahertz wave according to an embodiment of the present invention includes m identification units composed of: a terahertz wave transmission layer that is made of a material that transmits a terahertz wave; and a waveguide grating that resonates at a natural resonant frequency when receiving the transmitted terahertz wave, in which the natural resonant frequency is any one of a first natural resonant frequency to an n-th natural resonant frequency.

13 Claims, 20 Drawing Sheets

(51) Int. Cl.
<table>
<tr><td>G01N 21/17</td><td>(2006.01)</td></tr>
<tr><td>G01N 21/77</td><td>(2006.01)</td></tr>
<tr><td>G01N 21/90</td><td>(2006.01)</td></tr>
<tr><td>G06K 7/14</td><td>(2006.01)</td></tr>
<tr><td>B65D 25/20</td><td>(2006.01)</td></tr>
<tr><td>B65D 79/02</td><td>(2006.01)</td></tr>
<tr><td>B32B 27/00</td><td>(2006.01)</td></tr>
<tr><td>G06K 7/10</td><td>(2006.01)</td></tr>
<tr><td>B32B 7/12</td><td>(2006.01)</td></tr>
<tr><td>B32B 15/02</td><td>(2006.01)</td></tr>
<tr><td>B32B 3/06</td><td>(2006.01)</td></tr>
<tr><td>B65D 75/12</td><td>(2006.01)</td></tr>
</table>

(52) U.S. Cl.
CPC ............ *B32B 15/02* (2013.01); *B32B 15/043* (2013.01); *B32B 27/00* (2013.01); *B65D 25/205* (2013.01); *B65D 79/02* (2013.01); *G01N 21/17* (2013.01); *G01N 21/77* (2013.01); *G01N 21/90* (2013.01); *G06K 7/10564* (2013.01); *B32B 2255/06* (2013.01); *B32B 2255/26* (2013.01); *B32B 2307/204* (2013.01); *B32B 2307/418* (2013.01); *B32B 2307/732* (2013.01); *B32B 2439/70* (2013.01); *B65D 75/12* (2013.01); *B65D 2203/10* (2013.01); *G01N 2021/7769* (2013.01); *G01N 2201/061* (2013.01); *G01N 2201/068* (2013.01)

(56) References Cited

FOREIGN PATENT DOCUMENTS

KR 10-1128876 B1 3/2012
KR 10-2013-0077221 A 7/2013

* cited by examiner

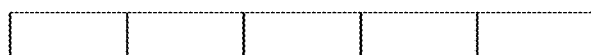
FIG. 14C
| $f_1 \sim f_n$ | $f_1 \sim f_n$ | $f_1 \sim f_n$ | $f_1 \sim f_n$ |
|---|---|---|---|
| $f_1 \sim f_n$ | $f_1 \sim f_n$ | $f_1 \sim f_n$ | $f_1 \sim f_n$ |
| $f_1 \sim f_n$ | $f_1 \sim f_n$ | $f_1 \sim f_n$ | $f_1 \sim f_n$ |
| $f_1 \sim f_n$ | $f_1 \sim f_n$ | $f_1 \sim f_n$ | $f_1 \sim f_n$ |
FIG. 14D
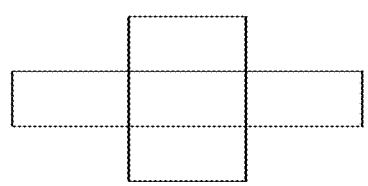
(a)
(b)
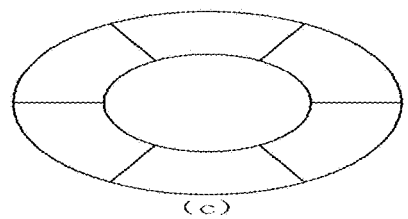
(c)
FIG. 14E

WRAPPER FOR TERAHERTZ, DETECTION SENSOR, DETECTION APPARATUS USING TERAHERTZ WAVE, OPTICAL IDENTIFICATION DEVICE FOR TERAHERTZ, APPARATUS FOR RECOGNIZING OPTICAL IDENTIFICATION DEVICE FOR TERAHERTZ WAVE, AND WRITING APPARATUS FOR IDENTIFICATION UNIT

TECHNICAL FIELD

The present invention relates to a wrapper for a terahertz wave that can detect a change in a packaging container using a non-destructive method using a terahertz wave and a structure for improving sensitivity, a detection sensor, and a detection apparatus using a terahertz wave.

The present invention relates to a optical identification device of which existence cannot be visually know because it has difficulty in checking information from visible light, ultraviolet rays, and near infrared rays, but it can check information only from terahertz waves.

BACKGROUND ART

Various packaging techniques have been used in accordance with the features of products to prevent decomposition, denaturation, and damage while the products are sent to consumers from manufacturers. However, accidents of decomposition or denaturation of the contents in products frequently occur due to carelessness in transportation and storage. Accordingly, there is a strong need of a detection method that can monitor the storage state of products at any time during transportation and methods of non-destructively examining the states inside packages have not been well known in the art. There have been proposed a method of indirectly examining the inside states of products by measuring the surface temperature of the products using an infrared camera or using a millimeter wave, but the existing non-destructive methods have a limit that it is impossible to measure small physical/chemical/biological changes in state or a small amount of foreign substances in objects or materials because the sensitivity is very low. For example, when detecting food poisoning bacteria in food that is transported after being packed, it is impossible to a small amount of change of the bacteria directly at the sites, so those bacteria are detected on the basis of indirect indexes through a microorganism proliferation modeling by measuring temperature using infrared rays. Accordingly, there is a limit in species, amount, and accuracy of harmful bacteria and the indirect index detection method has low sensitivity, so detection is made after microorganisms have already proliferated. Therefore, it is difficult to cope with this problem in advance.

At present, a barcode is widely used as an identification factor. In general, a barcode was proposed first in 'Calculation automation of supermarkets' by Wallace Flint in 1932, and at present, almost all articles are printed with barcodes, and purchase and sale of products are automatically managed by a POS (Point Of Sales system). Further, the usability has been rapidly increased with IT relating to post automation, factory automation, stock management, library, document management, and medical information. Recently, with the advent of a smartphone, applications that can search prices and the lowest price of products by reading out barcodes in real time have been developed.

Barcode signals are sets of continuous black modules and white modules, in which information is encoded in accordance with the widths and rations of the modules. It is required to restore the sizes of modules with in an allowable error range in order to accurately decode information.

However, since barcode signals are sets of continuous black modules and white modules, in which information is encoded in accordance with the widths and rations of the modules, it is impossible to encode a large amount of information in a limited space and to visually check the positions, so there is a limit in applying the barcode to security, anti-forgery, and the like.

DISCLOSURE

Technical Problem

An object of the present invention is to provide a technology of measuring physical/chemical/biological changes in a packaging container using a structure that can non-destructively improve detection sensitivity using terahertz waves.

Other objects and advantages of the present invention will be understood from the following description and will be made clearer by embodiments of the present invention. Further, it will be easily understood that the objects and advantages of the present invention can be accomplished by the configurations and combinations of them described in claims.

Another object of the present invention is to provide an optical identification device for terahertz waves that can show a large amount of identification codes in a small area by using m identification units including waveguide diffraction gratings having any one of n natural resonance frequencies and that can high-level security because it is impossible to visually recognize optical identification devices.

Other objects and advantages of the present invention will be understood from the following description and will be made clearer by embodiments of the present invention. Further, it will be easily understood that the objects and advantages of the present invention can be achieved by configurations or combinations of the configurations described in claims.

Technical Solution

A wrapper for a terahertz wave according to an embodiment of the present invention includes: a terahertz wave transmission layer that is made of a material that transmits a terahertz wave; and an electric field enhancement structure that enhances an electric field by reacting with a predetermined frequency band of terahertz waves passing through the terahertz wave transmission layer.

The wrapper for a terahertz wave may further include a filter layer that is combined with the electric field enhancement structure and passes only a specific material to the electric field enhancement structure.

The wrapper for a terahertz wave may further include: a selective detection layer that is combined with the electric field enhancement structure and bonds with only a specific material; and a filter layer that passes the specific material to the selective detection layer.

The wrapper for a terahertz wave may further include a terahertz wave shield layer that is formed on both sides of the terahertz wave transmission layer and the electric field enhancement structure and blocks a terahertz wave.

The electric field enhancement structure may be at least any one of a diffraction grating, a metal mesh, a metamaterial, a metal layer with an opening having a width equal to or smaller than the wavelength of a light source, a structure that induces surface plasmon resonance, and a photonic crystal structure.

A detection sensor for a terahertz wave that is inserted in a packaging container including a region that transmits a terahertz wave, according to another embodiment of the present invention, includes: a substrate that is made of a material transmitting a terahertz wave; and an electric field enhancement structure that is formed on the substrate and enhances an electric field by reacting with a predetermined frequency band of terahertz waves passing through the substrate.

The detection sensor for a terahertz wave may further include a filter layer that is combined with the electric field enhancement structure and passes only a specific material to the electric field enhancement structure.

The detection sensor for a terahertz wave may further include: a selective detection layer that is combined with the electric field enhancement structure and bonds with only a specific material; and a filter layer that passes the specific material to the selective detection layer.

The electric field enhancement structure may be at least any one of a diffraction grating, a metal mesh, a metamaterial, a metal layer with an opening having a width equal to or smaller than the wavelength of a light source, a structure that induces surface plasmon resonance, and a photonic crystal structure.

A detection apparatus using a terahertz wave according to another embodiment of the present invention includes: a wrapper for a terahertz wave including a terahertz wave transmission layer that is made of a material transmitting a terahertz wave, and an electric field enhancement structure that enhances an electric field by reacting with a predetermined frequency band of terahertz waves passing through the terahertz wave transmission layer; a terahertz light source that radiates a terahertz wave to the wrapper; and a detector that detects a characteristic of a terahertz wave generated from the wrapper.

The detection apparatus using a terahertz wave may further include a determiner that determines whether there is a change around the electric field enhancement structure by comparing the detected terahertz wave with a reference terahertz wave.

When a difference between the resonant frequency of the detected terahertz wave and the resonant frequency of the reference terahertz wave is over a predetermined range, the determiner may determine that there is a change around the electric field enhancement structure.

The wrapper may further include a filter layer that is combined with the electric field enhancement structure and passes only a specific material to the electric field enhancement structure.

The wrapper may further include: a selective detection layer that is combined with the electric field enhancement structure and bonds with only a specific material; and a filter layer that passes the specific material to the selective detection layer.

The wrapper may further include a terahertz wave shield layer that is formed on both sides of the terahertz wave transmission layer and the electric field enhancement structure and blocks a terahertz wave.

A detection apparatus using a terahertz wave according to another embodiment of the present invention includes: a detection sensor for a terahertz wave that is inserted in a packaging container including a region that transmits a terahertz wave, and includes a substrate that is made of a material that transmits a terahertz wave, and an electric field enhancement structure that is formed on the substrate and enhances an electric field by reacting with a predetermined frequency band of terahertz waves passing through the substrate; a terahertz light source that radiates a terahertz wave to the detection sensor; and a detector that detects a characteristic of a terahertz wave generated from the detection sensor.

The detection apparatus using a terahertz wave may further include a determiner that determines whether there is a change around the electric field enhancement structure by comparing the detected terahertz wave with a reference terahertz wave.

The detection sensor for a terahertz wave may further include a filter layer that is combined with the electric field enhancement structure and passes only a specific material to the electric field enhancement structure.

The detection sensor for a terahertz wave may further include: a selective detection layer that is combined with the electric field enhancement structure and bonds with only a specific material; and a filter layer that passes the specific material to the selective detection layer.

An optical identification device for a terahertz wave according to another embodiment of the present invention includes m identification units composed of: a terahertz wave transmission layer that is made of a material transmitting a terahertz wave; and a waveguide diffraction grating that resonates at a natural resonant frequency when the transmitted terahertz wave is radiated, in which the natural resonant frequency is any one of a first natural resonant frequency to an n-th natural resonant frequency.

The kinds of the natural resonant frequencies are n and the number of the identification units is m, so the optical identification device for a terahertz wave has $n^m$ available identification codes.

Arrangement of the identification units may mean identification information different from an identification code.

The identification units may be arranged in a shape of at least any one of a line, a circle, a rectangle, a lattice, and a cross.

An apparatus for recognizing an optical identification device for a terahertz wave according to another embodiment of the present invention includes: an optical identification device for a terahertz wave that includes m identification units, the units including a terahertz wave transmission layer that is made of a material that transmits a terahertz wave, and a waveguide diffraction grating that resonates at a natural resonant frequency when the transmitted terahertz wave is radiated, in which the natural resonant frequency is any one of a first natural resonant frequency to an n-th natural resonant frequency; a light source that radiates a terahertz wave to the optical identification device for a terahertz wave; and a detector that detects the natural resonant frequency of a terahertz wave generated from the optical identification device for a terahertz wave.

The apparatus for recognizing an optical identification device for a terahertz wave may further include a recognizing unit that recognizes identification codes on the basis of natural resonant frequencies detected for identification units, respectively.

The apparatus for recognizing an optical identification device for a terahertz wave may further include a light source-detector moving unit that moves the light source such that a terahertz wave generated from the light source is radiated sequentially to the identification units, and moves the detector as much as the movement of the light source.

The apparatus for recognizing an optical identification device for a terahertz wave may further include an optical identification device moving unit that moves the optical identification device for a terahertz wave such that a terahertz wave generated from the light source is radiated sequentially to the identification units.

The apparatus for recognizing an optical identification device for a terahertz wave may further include: a light source-detector moving unit that moves the light source in one direction and moves the detector as much as the movement of the light source; and an optical identification device moving unit that moves the optical identification device for a terahertz wave in another direction.

The light source may be a light source array including several light sources that can generate a terahertz wave, and the detector may be a detector array including several detectors matched with the light source array.

A writing apparatus for an identification unit according to another embodiment of the present invention includes: an identification unit including a terahertz wave transmission layer that is made of a material transmitting a terahertz wave and a waveguide diffraction grating that have different natural resonant frequencies a frequency band set for the transmitted terahertz wave; and a modulator that changes the natural resonant frequency of the waveguide diffraction grating to another natural resonant frequency in the set frequency band.

The modulator may change the natural resonant frequency of the waveguide diffraction grating to another natural resonant frequency within a predetermined frequency band by light radiation, heat application, or electricity supply.

Advantageous Effects

According to the present invention, it is possible to detect a change in a packaging container in real time at the site in a non-destructive way by using an electromagnetic wave at a terahertz wave band.

Further, it is possible to more accurately detect a change in a packaging container by using a structure that can improve detection degree in a non-destructive method, using a terahertz wave.

According to the present invention, since it is possible to one identification unit can express n, it is possible to express a large amount of identification codes in a small area using less identification units.

Further, since the optical identification device for a terahertz wave cannot visually checked in visible light and infrared ray regions, security is high, so it can be used in various fields.

Further, there is no need for manufacture an identification unit for each resonant frequency, so it is possible to reduce the manufacturing cost of an identification unit and an optical identification device.

Further, since a user generates an identification code by changing an identification unit to a desired resonant frequency at the site using the writing apparatus for an identification unit, convenience for the user can be improved.

DESCRIPTION OF DRAWINGS

FIGS. 14A to 14E are views illustrating in detail an optical identification device for a terahertz wave according to an embodiment of the present invention.

BEST MODE

Hereinafter, the present invention will be described in detail with reference to the accompanying drawings.

Figure 1:
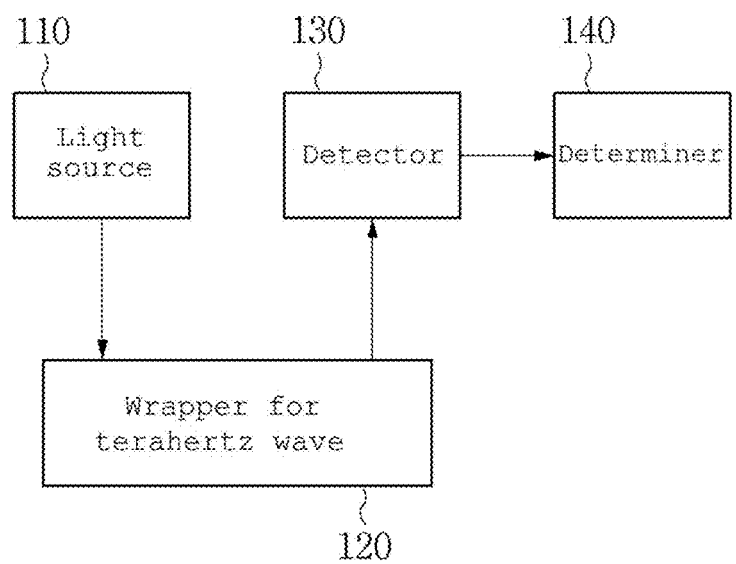
FIG. 1 is a block diagram of a detection apparatus using a terahertz wave according to an embodiment of the present invention.

FIG. 1 is a block diagram of a detection apparatus using a terahertz wave according to an embodiment of the present invention.

Referring to FIG. 1, a detection apparatus 100 using a terahertz wave includes a light source 110, wrapper for a terahertz wave 120, a detector 130, and a determiner 140.

The light source 110 can radiate terahertz waves to the wrapper 120. For example, various devices that can generate terahertz waves may be the light source 110. A terahertz wave, which is an electromagnetic wave between the infrared ray and the microwave, may generally have a frequency of 0.1 THz to 10 THz. However, even if it comes a little out of this range, it may be considered as the terahertz wave stated herein if it can be easily found by those skilled in the art.

The wrapper 120 for a terahertz wave may include a terahertz wave transmission layer made of a material that transmits a terahertz wave, an electric field enhancement structure that enhances an electric field by reacting with a predetermined frequency band of terahertz waves passing through the terahertz wave transmission layer, a selective detection layer that bonds only with specific materials, and a filter layer that transmits only specific materials to the selective detection layer. This will be described below.

The detector 130 can detect characteristics of a terahertz wave generated from the wrapper 120 for a terahertz wave. For example, the detector 130 can detect characteristics of a terahertz wave that is reflected, transmitted, diffracted, and dispersed from the wrapper 120 for a terahertz wave. In detail, for example, the detector 130 can detect the intensity or the resonant frequency of a terahertz wave created from the wrapper 120 for a terahertz wave.

The determiner 140 can determine whether there is a change around an electric field enhancement structure included in the wrapper 120 for a terahertz wave by comparing a terahertz wave detected by the detector 130 with a reference terahertz wave. The change may include physical/chemical/biological changes. The physical change may mean a change in temperature, volume, and shape, the chemical change may mean a quantitative change in component such as a material, gas, and water, and the biological change may mean the number of individuals such as a microorganism, a virus, and a mold. The degree of a change may be determined on the basis of the difference between the resonant frequency of a detected terahertz wave and the resonant frequency of a reference terahertz wave.

For example, when the difference between the resonant frequency of a terahertz wave detected by the detector 130 and the resonant frequency of a reference terahertz wave is over a predetermined range, the determiner 140 can determine that there is a change around the electric field enhancement structure included in the wrapper 120 for a terahertz wave.

Further, for example, the determiner 140 can determine that there is a change around the electric field enhancement structure included in the wrapper 120 for a terahertz wave on the basis of the difference between the resonant frequency of a detected terahertz wave and the resonant frequency of a reference terahertz wave. In detail, for example, the determiner 140 may determine the degree of a physical/chemical/biological change around the electric field enhancement structure on the basis of the difference.

Further, for example, the determiner 140 compares the intensity of the terahertz wave detected by the detector 130 at a specific wavelength with the intensity of a reference terahertz wave, and when the difference between the intensity of the terahertz wave detected by the detector 130 at a specific wavelength and the intensity of the reference terahertz wave is over a predetermined range, the determiner 140 can determine that there is a change in the electric field enhancement structure included in the wrapper 120 for a terahertz wave.

The detection apparatus using a terahertz wave can detect a change in a packaging container in real time at the site in a non-destructive method by using an electromagnetic wave at a terahertz wave band.

Further, the detection apparatus using a terahertz wave can more accurately detect a physical/chemical/biological change in a packaging container by using a structure that can improve detection degree in a non-destructive method, using a terahertz wave.

Figure 2:
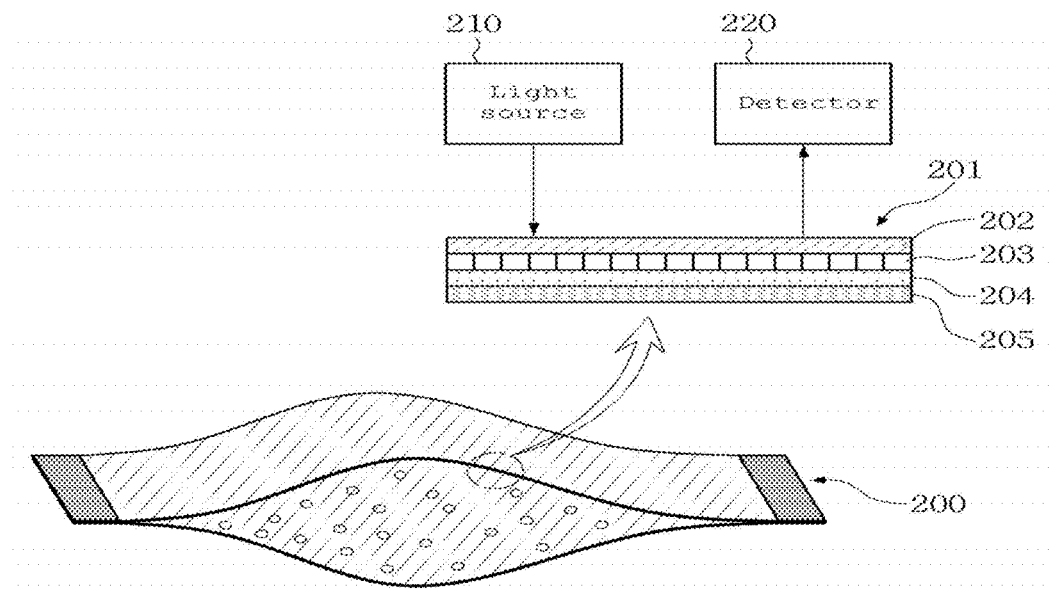
FIG. 2 is a view illustrating a wrapper for a terahertz wave according to an embodiment of the present invention.

FIG. 2 is a view illustrating a wrapper for a terahertz wave according to an embodiment of the present invention.

Referring to FIG. 2, a packaging container 200 having a region that transmits a terahertz wave may include a space surrounded by a wrapper 201 for a terahertz wave. A substance such as food can be inserted in the space.

The wrapper 201 for a terahertz wave may include a terahertz wave transmission layer 202, an electric field enhancement structure 203, a selective detection layer 204, and a filter layer 205.

The terahertz wave transmission layer 202 is made of a material that transmits a terahertz wave.

The electric field enhancement structure 203 can enhance an electric field by reacting with a predetermined frequency band of terahertz waves passing through the terahertz wave transmission layer 202. For example, the electric field enhancement structure 203 may have various structures that can enhance an electric field such as a diffraction grating, a metal mesh, a metamaterial, a metal layer having an opening having a width equal to or smaller than the wavelength of a light source, a structure that induces surface plasmon resonance, and a photonic crystal structure. The opening may be a slit or a hole.

The selective detection layer 204 may be a layer that bonds with only specific materials. For example, the selective detection layer 204 may be a layer formed by fixing a sensing material that bonds with specific materials to a support. Herein, the sensing material may be a material that bonds with only specific materials to be detected.

For example, when the specific material is a specific ion, a specific gas, water, or a harmful material, the selective detection layer 204 may bond with only the specific ion, specific gas, water, and harmful material, and may not bond with other materials. Herein, the specific material means an object material to be detected.

Further, the selective detection layer 204 may be a layer that senses a change in physical environment such as temperature and volume of a package. For example, when there is a change in temperature or volume of a package, a change selectively occurs with the change in temperature or volume, and when there is no physical change in temperature or volume of a package, the selective detection layer may not change.

The filter layer 205 can pass only specific materials to the selective detection layer 204. For example, the filter layer 205 may be formed at the innermost portion of the packaging container 200 and can pass only specific materials (for example, a specific ion, a specific gas, water, and a harmful material) in various materials existing in the packaging container 200 to the selective detection layer 204.

In order to detect a specific gas change in the packaging container 200, the selective detection layer 204 may be a layer that can bond with the specific gas and the filter layer 205 may be a layer that can pass only gas. For example, when the light source 210 radiates a terahertz wave to the wrapper 201, the detector 220 can detect the resonant frequency of a terahertz wave generated from the wrapper 201 for a terahertz wave. The determiner (not illustrated)

compares the resonant frequency of a terahertz wave generated by the wrapper 201 for a terahertz wave with the resonant frequency of a reference wrapper 201 for a terahertz wave (resonant frequency when there is no water), and when the difference between the resonance frequencies is larger than a predetermined range, the determiner can determine that a specific gas was adsorbed around the electric field enhancement structure. That is, the determiner (not illustrated) can determine that a specific gas was generated in the packaging container 200. The predetermined range may be set at various levels by a user, and the like.

The determiner (not illustrated) compares the resonant frequency of a terahertz wave detected by the detector 220 with the resonant frequency of a reference terahertz wave (resonant frequency when a specific gas is not adsorbed), and when the difference between the resonance frequencies is over a predetermined range, the determiner can determine that a specific gas was adsorbed around the electric field enhancement structure. That is, the determiner (not illustrated) can determine that a specific gas was produced in the packaging container 200. The predetermined range may be set at various levels by a user, and the like.

As another example, in order to detect a change in water in the packaging container 200, the selective detection layer 204 may be a layer that can bond with water and the filter layer 205 may be a layer that can pass only water. For example, when the light source 210 radiates a terahertz wave to the wrapper 201, the detector 220 can detect the resonant frequency of a terahertz wave generated from the wrapper 201 for a terahertz wave. The determiner (not illustrated) compares the resonant frequency of a terahertz wave generated from the wrapper 201 for a terahertz wave with the resonant frequency of a reference terahertz wave (resonant frequency when there is no water), and when the difference between the resonance frequencies is over a predetermined range, the determiner can determine that water was produced around the electric field enhancement structure. That is, the determiner (not illustrated) can determine that water is produced in the packaging container 200. The predetermined range may be set at various levels by a user, and the like.

The determiner (not illustrated) compares the resonant frequency of a terahertz wave detected by the detector 220 with the resonant frequency of a reference terahertz wave (resonant frequency when there is no water), and when the difference between the resonance frequencies is over a predetermined range, the determiner can determine that water was produced around the electric field enhancement structure. That is, the determiner (not illustrated) can determine that water was produced in the packaging container 200. The predetermined range may be set at various levels by a user, and the like.

As another example, in order to detect a temperature change inside the packaging container 200, the selective detection layer 204 may be a layer including thermochromic dye that is sensitive to heat and the filter layer 205 may be a layer that passes only air and has low heat transfer rate. For example, when the light source 210 radiates a terahertz wave to the wrapper 201, the detector 220 can detect the resonant frequency of a terahertz wave generated from the wrapper 201 for a terahertz wave. The determiner (not illustrated) compares the resonant frequency of a terahertz wave generated from the wrapper 201 for a terahertz wave with the resonant frequency of a reference terahertz wave (resonant frequency at reference temperature), and when the difference between the resonance frequencies is over a predetermined range, the determiner can determine that there is a temperature change around the electric field enhancement structure, and can check the internal temperature of the package by checking the temperature change due to predetermined differences of resonance frequencies. That is, the determiner (not illustrated) can determine whether there is a temperature change in the packaging container 200. The predetermined range may be set at various levels by a user, and the like.

The determiner (not illustrated) compares the resonant frequency of a terahertz wave detected by the detector 220 with the resonant frequency of a reference terahertz wave (resonant frequency at reference temperature), and when the difference between the resonance frequencies is over a predetermined range, the determiner can determine that there is a temperature change around the electric field enhancement structure. That is, the determiner (not illustrated) can determine whether there is a temperature change in the packaging container 200. The predetermined range may be set at various levels by a user, and the like.

Figure 3:
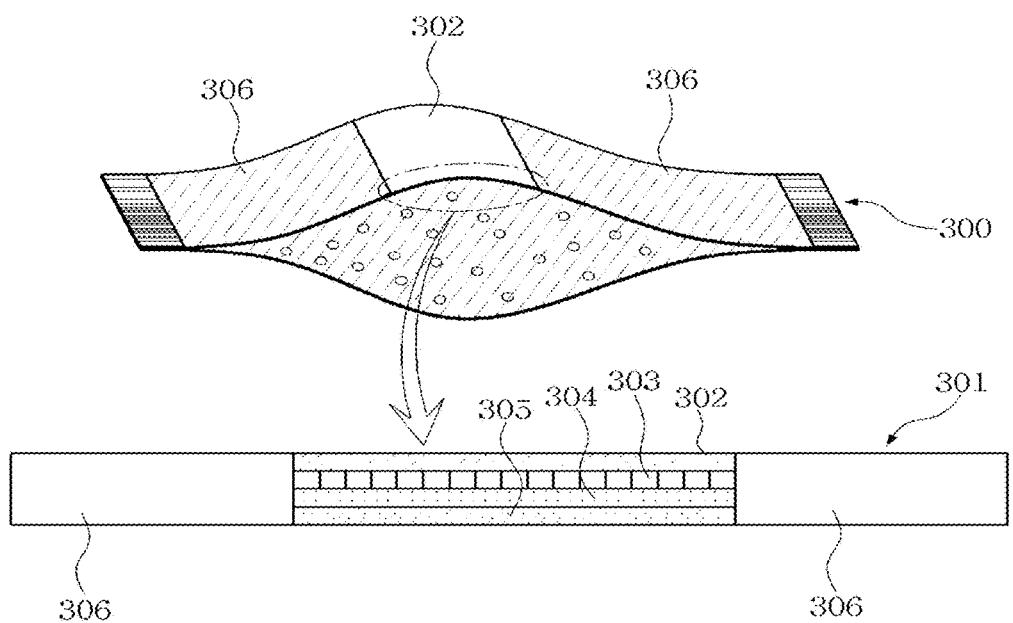
FIG. 3 is a view illustrating a wrapper for a terahertz wave according to another embodiment of the present invention.

FIG. 3 is a view illustrating a wrapper for a terahertz wave according to another embodiment of the present invention.

Referring to FIG. 3, a packaging container 300 having a region that transmits a terahertz wave may include a space surrounded by a wrapper 301 for a terahertz wave. A substance such as food can be inserted in the space.

The wrapper 301 for a terahertz wave may include a terahertz wave transmission layer 302, an electric field enhancement structure 303, a selective detection layer 304, a filter layer 305, and a terahertz wave shield layer 306. As illustrated in FIG. 3, the wrapper 301 for a terahertz wave may include the terahertz wave transmission layer 302 that can pass a terahertz wave and the terahertz wave shield layer 306 that blocks a terahertz wave, and the shapes and the sizes of the ranges of the terahertz wave transmission layer 302 and the terahertz wave shield layer 306 may be changed in various ways. As described above, a range that transmits a terahertz wave may be formed not at the entire, but at a portion of the packaging container 300.

The terahertz wave transmission layer 302 is made of a material that transmits a terahertz wave.

The electric field enhancement structure 303 can enhance an electric field by reacting with a predetermined frequency band of terahertz waves passing through the terahertz wave transmission layer 302. For example, the electric field enhancement structure 303 may have various structures that can enhance an electric field such as a diffraction grating, a metal mesh, a metamaterial, a metal layer having an opening having a width equal to or smaller than the wavelength of a light source, a structure that induces surface plasmon resonance, and a photonic crystal structure.

The selective detection layer 304 may be a layer formed by fixing a sensing material that bonds with specific materials to a support. For example, when the specific material is a specific ion, a specific gas, water, or a harmful material, the selective detection layer 304 may bond with only the specific ion, specific gas, water, and harmful material, and may not bond with other materials.

The filter layer 305 can pass only a specific material to the selective detection layer 304. For example, the filter layer 305 may be formed at the innermost portion of the packaging container 300 and can pass only specific materials (for example, a specific ion, a specific gas, water, and a harmful material) in various materials existing in the packaging container 300 to the selective detection layer 304.

The terahertz wave shield layer 306 is formed on both sides of the terahertz wave transmission layer 302, the electric field enhancement structure 303, the selective detection layer 30, and the filter layer 305, and can reflect a terahertz wave.

The terahertz wave shield layer 306, which is formed by coating a polymeric packing material (polyethylene; PE, polypropylene; PP) with a metallic layer such as an aluminum layer in order to protect a product from ultraviolet rays, visible light, infrared rays, water, and a harmful material that flows into a package from the outside, include metallic components and reflects a terahertz wave.

In order to easily detect the inside of a wrapper in a non-destructive method, a sensing window composed of the terahertz wave transmission layer 302, electric field enhancement structure 303, selective detection layer 304, and filter layer 305 may be formed only at a specific area of the entire wrapper.

Figure 4:
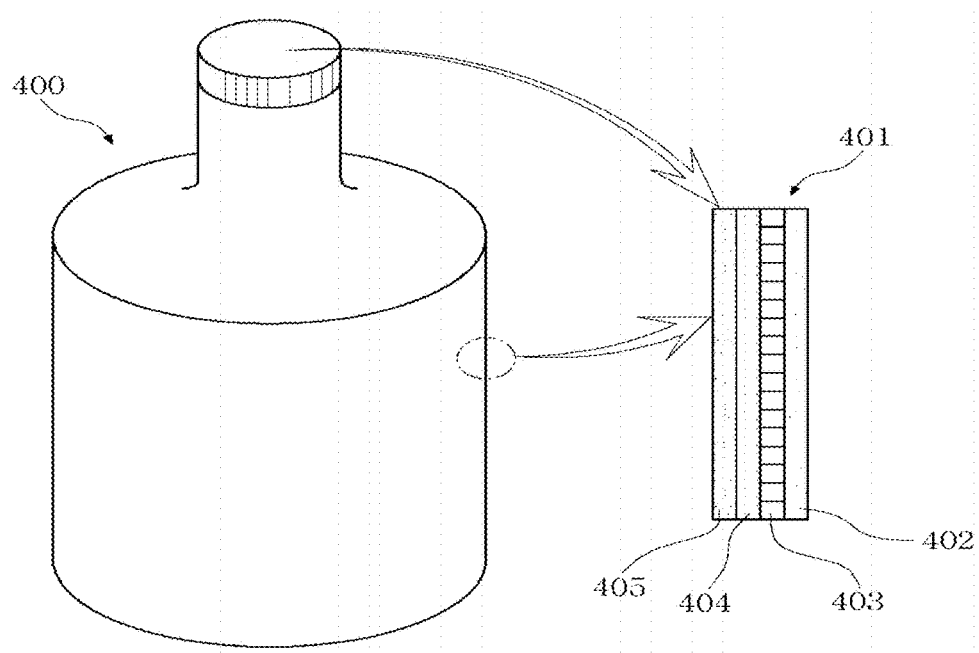
FIG. 4 is a view illustrating a wrapper for a terahertz wave according to another embodiment of the present invention.

FIG. 4 is a view illustrating a wrapper for a terahertz wave according to another embodiment of the present invention.

Referring to FIG. 4, a packaging container 400 having a region that transmits a terahertz wave may be a container for keeping a drink. A portion of the side of the packaging container 400 or the cap may be made of a wrapper 401 for a terahertz wave. As described above, a range that transmits a terahertz wave may be formed not at the entire, but at a portion of the packaging container 400.

The wrapper 401 for a terahertz wave may include a terahertz wave transmission layer 402, an electric field enhancement structure 403, a selective detection layer 404, and a filter layer 405.

The terahertz wave transmission layer 402 is made of a material that transmits a terahertz wave.

The electric field enhancement structure 403 can enhance an electric field by reacting with a predetermined frequency band of terahertz waves passing through the terahertz wave transmission layer 402. For example, the electric field enhancement structure 403 may have various structure that can enhance an electric field such as a diffraction grating, a metal mesh, a metamaterial, a metal layer having an opening having a width equal to or smaller than the wavelength of a light source, a structure that induces surface plasmon resonance, and a photonic crystal structure.

The selective detection layer 404 may be a layer formed by fixing a sensing material that bonds with specific materials to a support. For example, when the specific material is a specific ion, a specific gas, water, or a harmful material, the selective detection layer 404 may bond with only the specific ion, specific gas, water, and harmful material, and may not bond with other materials.

The filter layer 405 can pass only specific materials to the selective detection layer 304. For example, the filter layer 405 may be formed at the innermost portion of the packaging container 400 and can pass only specific materials (for example, a specific ion, a specific gas, water, and a harmful material) in various materials existing in the packaging container 400 to the selective detection layer 304.

Figure 5:
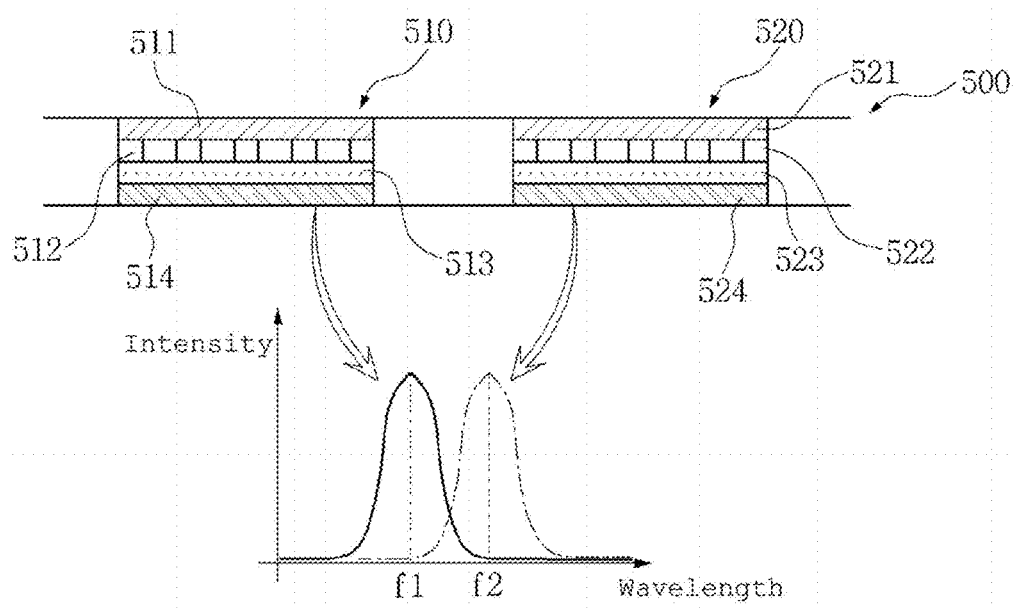
FIG. 5 is a view illustrating a wrapper for a terahertz wave according to another embodiment of the present invention.

FIG. 5 is a view illustrating a wrapper for a terahertz wave according to another embodiment of the present invention.

Referring to FIG. 5, a wrapper 500 for a terahertz wave may include a first range 510 that can obtain a reference terahertz wave characteristic and a second range that can obtain a modified terahertz wave characteristic.

The first region 510 may include a terahertz wave transmission layer 511, an electric field enhancement structure 512, a selective detection layer 513 not including a sensing material, and a filter layer 514.

The second region 520 may include a terahertz wave transmission layer 521, an electric field enhancement structure 522, a selective detection layer 523 including a sensing material, and a filter layer 524.

The functions of the layers in the regions were described above, so they are not described here.

When a light source (not illustrated) radiates a terahertz wave to the first region 510, a detector (not illustrated) can detect the first resonant frequency f1 of the terahertz wave detected at the first region 510. Herein, the first resonant frequency f1 is the resonant frequency of a reference terahertz wave. When the light source (not illustrated) radiates a terahertz wave to the second region 520, the detector (not illustrated) can detect the second resonant frequency f2 of the terahertz wave detected at the second region 520. Herein, the second resonant frequency is the resonant frequency of a terahertz wave changed by bonding of a specific material and the sensing material in the selective detection layer 523. In other words, when a specific material bonds with the selective detection layer 523, the second resonant frequency f2 changes.

A determiner (not illustrated) compares the first resonant frequency f1 of a terahertz wave detected at the first region 510 (resonant frequency of a reference terahertz wave) with the second resonant frequency f2 of the terahertz wave detected at the second region 520, and when the difference between the resonance frequencies is over a predetermined range, the determiner can determine that there was a physical/chemical/biological change in a packaging container (not illustrated).

Figure 6:
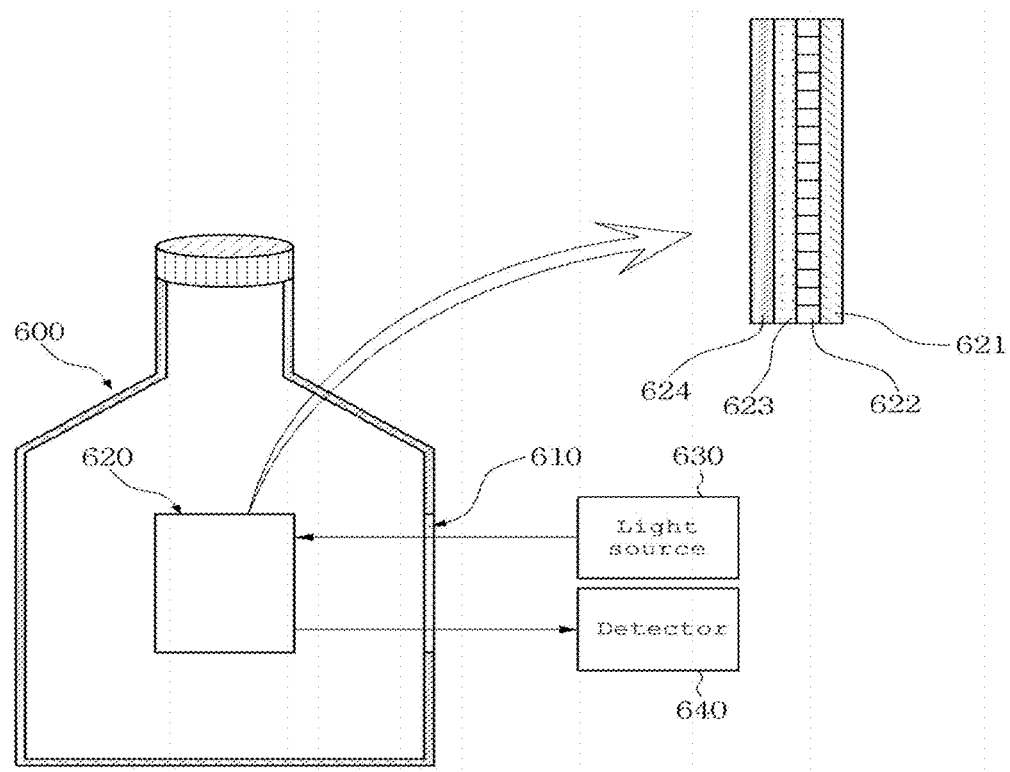
FIG. 6 is a view illustrating a detection sensor for a terahertz wave according to an embodiment of the present invention.

FIG. 6 is a view illustrating a detection sensor for a terahertz wave according to an embodiment of the present invention.

Referring to FIG. 6, a packaging container 600 having a region that transmits a terahertz wave may be a container for keeping a drink. The packaging container 600 may include a region 610 that transmits a terahertz wave at a portion of the side.

A detection sensor 620 for a terahertz wave may include a substrate layer 621, an electric field enhancement structure 622, a selective detection layer 623, and a filter layer 624.

The substrate layer 621 is made of a material that transmits a terahertz wave.

The electric field enhancement structure 622 can enhance an electric field by reacting with a predetermined frequency band of terahertz waves passing through the substrate layer 621. For example, the electric field enhancement structure 622 may have various structures that can enhance an electric field such as a diffraction grating, a metal mesh, a metamaterial, a metal layer having an opening having a width equal to or smaller than the wavelength of a light source, a structure that induces surface plasmon resonance, and a photonic crystal structure.

The selective detection layer 623 may be a layer formed by fixing a sensing material that bonds with specific materials to a support. For example, when the specific material is a specific ion, a specific gas, water, or a harmful material, the selective detection layer 623 may bond with only the specific ion, specific gas, water, and harmful material, and may not bond with other materials.

The filter layer 624 can pass only specific materials to the selective detection layer 623. For example, the filter layer 624 may be formed at the innermost portion of the packaging container 600 and can pass only specific materials (for example, a specific ion, a specific gas, water, and a harmful material) in various materials existing in the packaging container 600 to the selective detection layer 623.

In order to detect a change in water in the packaging container 600, the selective detection layer 623 may be a layer that can bond with water and the filter layer 624 may be a layer that can pass only water. For example, when the light source 630 radiates a terahertz wave to the detection sensor 620, the detector 640 can detect the resonant frequency of a terahertz wave detected by the detection sensor 620. The determiner (not illustrated) compares the resonant frequency of a terahertz wave detected by the detection sensor 620 with the resonant frequency of a reference terahertz wave (resonant frequency when there is no water), and when the difference between the resonance frequencies is over a predetermined range, the determiner can determine that water was produced around the electric field enhancement structure. That is, the determiner (not illustrated) can determine that water was produced in the packaging container 600.

Figures 7A, 7B:
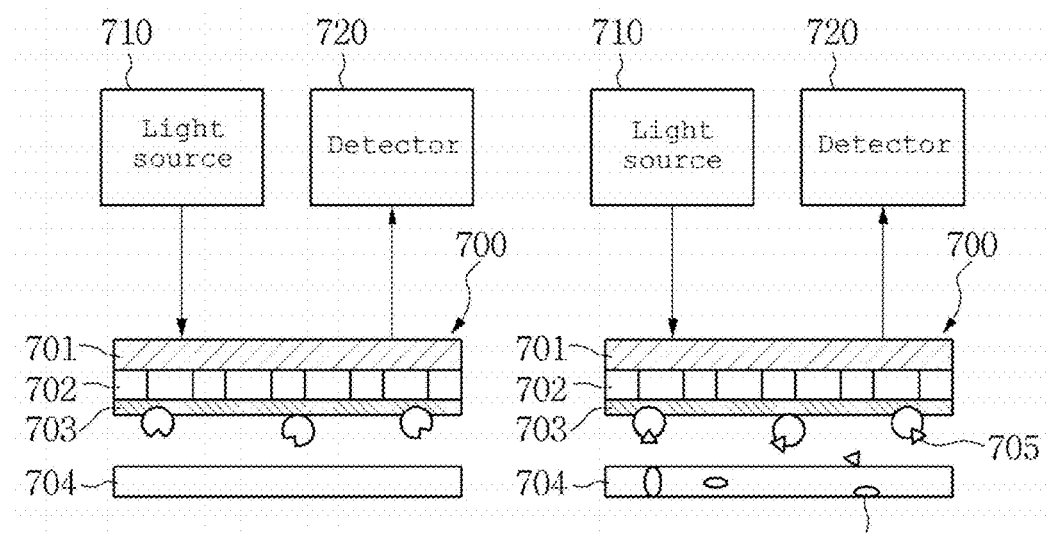
FIGS. 7A to 7C are views illustrating a resonant frequency that is changed due to bonding of a specific material to a selective detection layer according to an embodiment of the present invention.
Figure 7C:
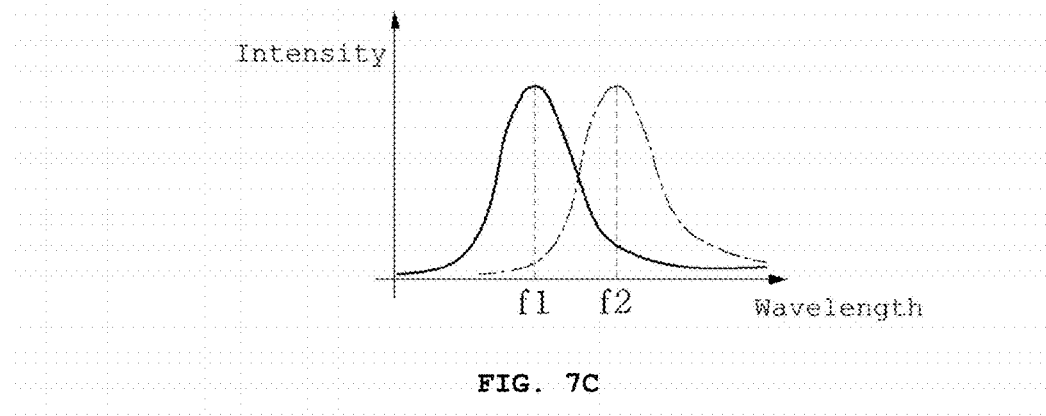

FIGS. 7A to 7C are views illustrating a resonant frequency that is changed due to bonding of a specific material to a selective detection layer according to an embodiment of the present invention.

Referring to FIGS. 7A and 7B, a wrapper 700 for a terahertz wave may include a terahertz wave transmission layer 701, an electric field enhancement structure 702, a selective detection layer 703, and a filter layer 704.

The terahertz wave transmission layer 701 is made of a material that transmits a terahertz wave.

The electric field enhancement structure 702 can enhance an electric field by reacting with a predetermined frequency band of terahertz waves passing through the terahertz wave transmission layer 701. For example, the electric field enhancement structure 702 may have various structure that can enhance an electric field such as a diffraction grating, a metal mesh, a metamaterial, a metal layer having an opening having a width equal to or smaller than the wavelength of a light source, a structure that induces surface plasmon resonance, and a photonic crystal structure.

The selective detection layer 703 may be a layer formed by fixing a sensing material that bonds with a specific material 705 to a support. For example, when the specific material is a specific ion, a specific gas, water, or a harmful material, the selective detection layer 703 may be combined with only the specific ion, specific gas, water, and harmful material, and may not be combined with other materials.

The filter layer 704 can pass only a specific material 705 to the selective detection layer 704. For example, the filter layer 704 may be formed at the innermost portion of the packaging container and can pass only specific materials (for example, a specific ion, a specific gas, and water) in various materials existing in the packaging container to the selective detection layer 703.

Water is not bonded to the selective detection layer 703 in FIG. 7A, while water is bonded to the selective detection layer 703 in FIG. 7B. It is assumed hereafter that a change of water in a packaging container is detected. In this case, the selective detection layer 703 can bond only with water 705 and the filter layer 704 can pass only water and block other materials 706.

In FIG. 7A, when a light source 710 radiates a terahertz wave to the wrapper 700, the detector 720 can detect the first resonant frequency f1 of the terahertz wave detected from the wrapper 700 for a terahertz wave. Herein, the first resonant frequency f1 is the resonant frequency of a reference terahertz wave.

In FIG. 7B, when the light source 710 radiates a terahertz wave to the wrapper 700, the detector 720 can detect the second resonant frequency f2 of the terahertz wave detected from the wrapper 700 for a terahertz wave. As water 705 is bonded to the selective detection layer 703, the characteristic of the electric field enhancement structure 702 changes, so the second resonant frequency f2 changes differently from the first resonant frequency of a reference terahertz wave.

A determiner (not illustrated) compares the first resonant frequency f1 of the terahertz wave obtained in FIG. 7A (resonant frequency of a reference terahertz wave) with the second resonant frequency f2 of the terahertz wave obtained in FIG. 7B, and when the difference between the resonant frequencies is over a predetermined range, the determiner can determine that water was produced in the packaging container (not illustrated).

Figure 8A:
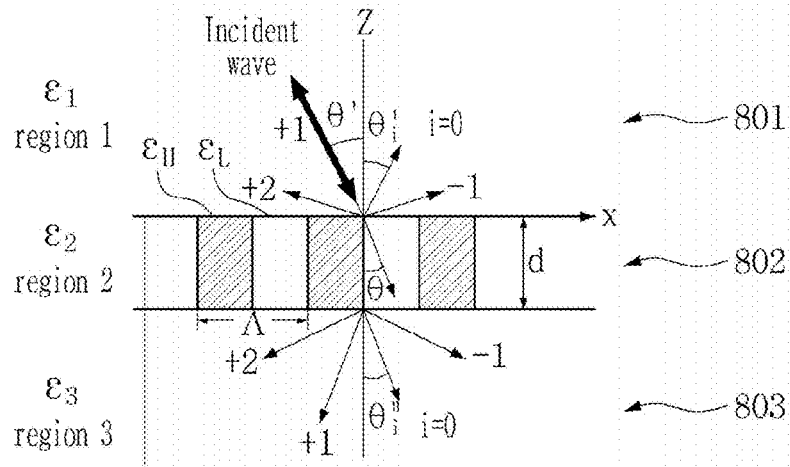
FIGS. 8A to 8C are views illustrating an electric field enhancement structure according to an embodiment of the present invention.
Figure 8B:
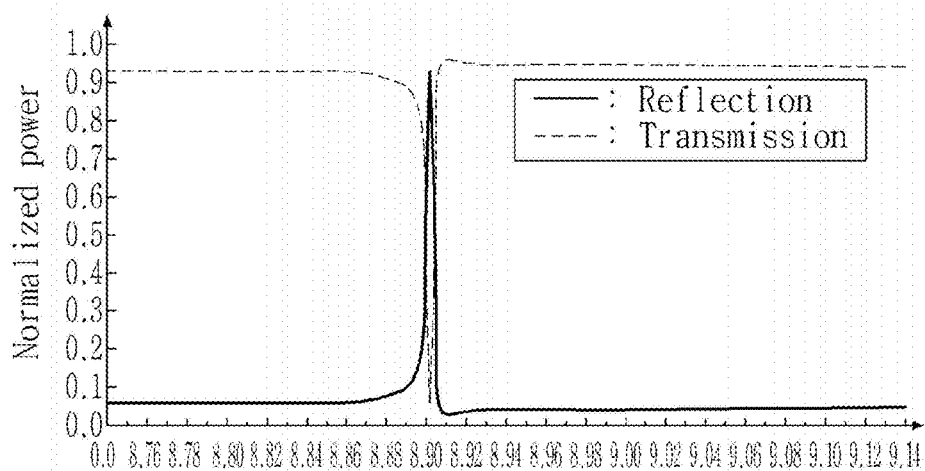
Figure 8C:
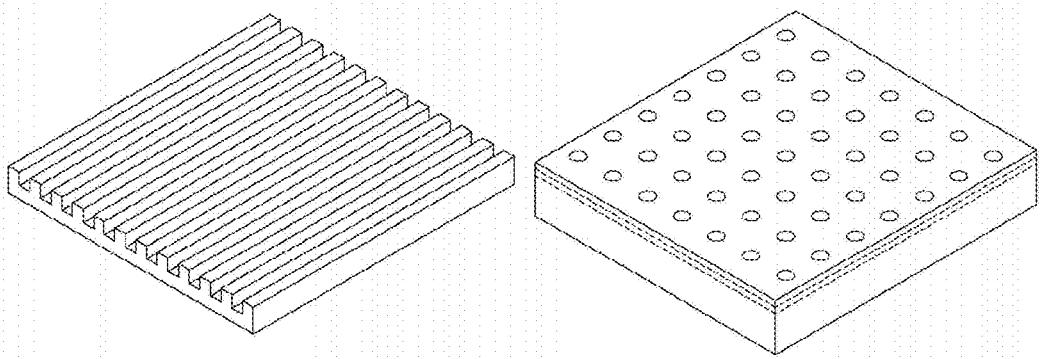

FIGS. 8A to 8C are views illustrating an electric field enhancement structure according to an embodiment of the present invention.

Referring to FIG. 8A, an electric field enhancement structure may be a waveguide diffraction grating that causes GMR (Guided Mode Resonance) at a specific wavelength.

The waveguide diffraction grating 802 can diffract incident light under given conditions (the wavelength of incident light, an incident angle, the thickness and effective refractive index of a waveguide, and the like). Except for the zeroth-order, high-order diffractive waves can generate a guided mode in the waveguide diffraction grating 802. In this case, a zeroth-order reflected wave-transmitted wave make phase matching with the guided mode and the energy of the guided mode generates resonance transmitted back to the zeroth-order reflected wave-transmitted wave. With the resonance, a zeroth-order reflected-diffracted wave is 100% reflected due to constructive interference and the zeroth-order transmitted-diffracted wave is 0% transmitted by offset interference, so a very sharp resonance curve is constructed at a specific wavelength band.

FIG. 8B illustrates a GMR result in which a diffraction grating ($n_H$=1.80, $n_L$=1.72, thickness=80 um, cycle=200 um) is made of SU-8 photoresist on a transparent polymethylpentene substrate (n=1.46) at a terahertz band and is calculated by FDM (resonance is generated at 0.89 THz).

As illustrated in FIG. 8A, assuming that the permittivity of a cover layer 810 is $\varepsilon_1$, the permittivity of a waveguide diffraction grating layer 802 is $\varepsilon_2$, and the permittivity of a substrate layer 803 is $\varepsilon_3$, the permittivity $\varepsilon_2$ of a waveguide diffraction grating layer can be expressed as in the following equation.

$$\varepsilon_2(X)=\varepsilon_g+\Delta\varepsilon*\cos(Kx) \qquad \text{[Equation]}$$

where $\varepsilon_g$ is the average of two permittivities ($\varepsilon_H$, $\varepsilon_L$) constituting a diffraction grating and repeated, $\Delta\varepsilon$ is the maximum change of permittivity, K is the frequency of a grating, $2\pi/\Lambda$, $\Lambda$ is the cycle of a grating, and x is the distance from the origin in the X-axial direction.

In this case, the effective permittivity N of a waveguide has only to satisfy the following condition so that a waveguide diffraction grating resonates at a specific wavelength and incident angle of incident light, that is, a waveguide mode is generated.

$$\max(\sqrt{\varepsilon_1},\sqrt{\varepsilon_2})|N|<\sqrt{\varepsilon_g}$$

A phenomenon that when GMR is generated in a waveguide g diffraction grating, an electric field is concentrated around the diffraction grating has been well known and a fine change in permittivity around the waveguide diffraction grating is entirely exhibited as a resonant frequency due to the near field enhancement. Using this principle, a sensing film is formed by the waveguide diffraction grating and chemical-physical bonding of a fine sensing material generated in the sensing film is exhibited as a change of a resonant frequency, so it can be used as high-sensitivity sensing principle.

It is possible to make of a terahertz wave sensing device having high sensitivity by forming a GMR sensing device that reacts in a terahertz wave region in a wrapper by applying this principle to the terahertz wave region. In particular, non-destructive detection with high sensitivity can be achieved by combination with the non-destructive characteristic of a terahertz wave.

FIG. 8C is a perspective view illustrating the structure and shape of a waveguide diffraction grating.

The diffraction grating may include grooves or ridges on a dielectric slab. Further, for example, the diffraction grating is a flat dielectric sheet having permittivity (for example, a phase grating) that periodically alternate in a dielectric sheet. The phase grating may be formed in a dielectric sheet by forming array of periodic holes passing through the dielectric sheet.

As another example, the diffraction grating may include any one of a one-dimensional (1D) diffraction grating and a two-dimensional diffraction grating. The 1D diffraction grating, for example, may include a set of actually straight grooves that are periodic and parallel only in a first direction (for example, x-axial direction). The 2D diffraction grating, for example, may include an array of holes in a dielectric slab or sheet, in which the holes are periodically spaced in two perpendicular directions (for example, in both of x-axial and y-axial directions). The 2D diffraction grating is also called a photonic crystal.

Figure 9A:
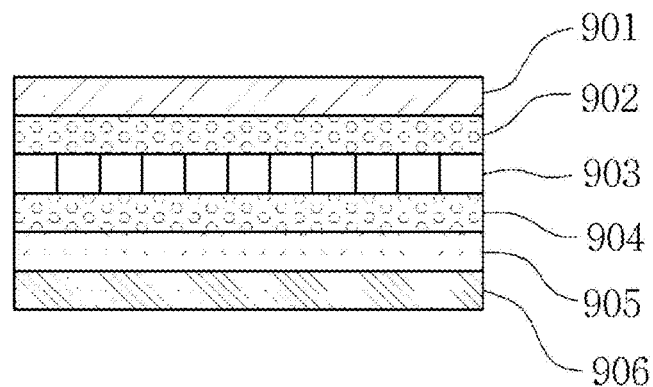
FIGS. 9A to 9C are views illustrating a modification of a wrapper including an electric field enhancement structure according to an embodiment of the present invention.
Figure 9B:
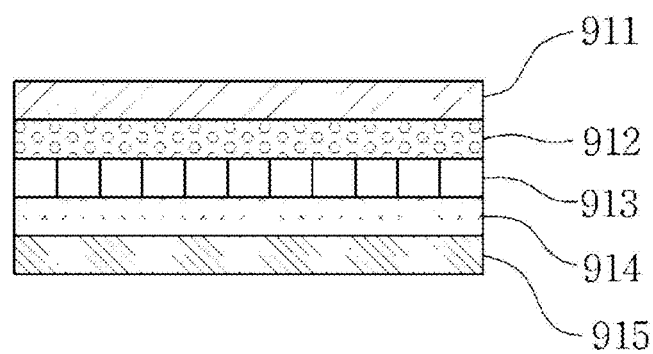
Figure 9C:
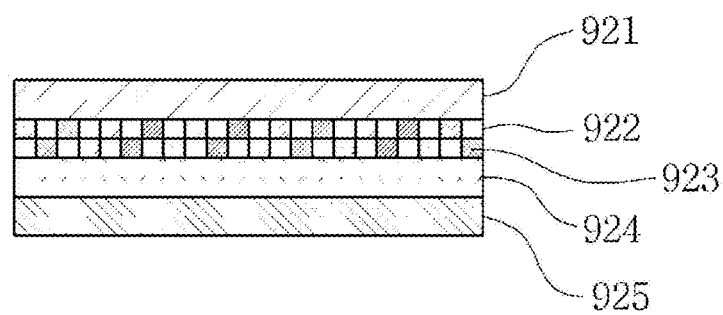
Figure 10A:
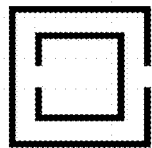
FIGS. 10A to 10J are views illustrating an electric field enhancement structure according to an embodiment of the present invention.
Figure 10B:
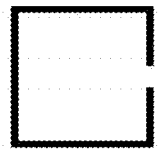
Figure 10C:
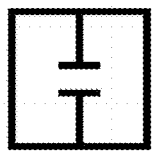
Figure 10D:
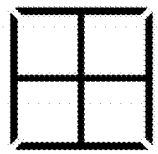
Figure 10E:
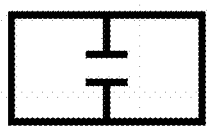
Figure 10F:
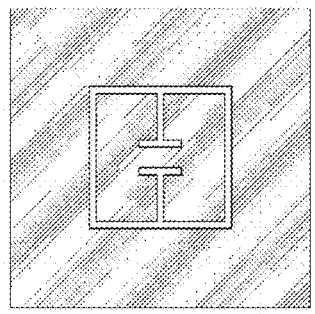
Figure 10G:
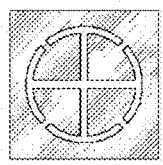
Figure 10H:
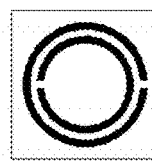
Figure 10I:
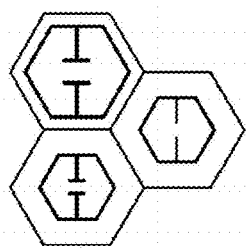
Figure 10J:
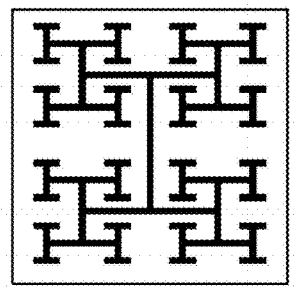

FIGS. 9A to 9C are views illustrating a modification of a wrapper including an electric field enhancement structure according to an embodiment of the present invention.

Referring to FIG. 9A, a wrapper for a terahertz wave may include a terahertz wave substrate layer 901, a first dielectric layer 902, a waveguide diffraction grating layer 903, a second dielectric layer 904, a selective detection layer 905, and a filter layer 906.

Referring to FIG. 9A, the waveguide diffraction grating layer 903 is covered with the dielectric layers 902 and 904 over and under it. In this case, a sideband around peaks of a resonance curve is decreased and an anti-reflection condition is determined by the thickness of a dielectric. That is, the waveguide diffraction grating layer 903 has a thickness corresponding to a half the resonance wavelength and the upper and lower dielectric layer 902 and 904 are designed to have a thickness that is a quarter of the resonance wavelength. In this case, the refractive indexes of the dielectric layers 902 and 904 should be all smaller than the effective refractive index of the waveguide diffraction grating layer 903.

Referring to FIG. 9B, a wrapper for a terahertz wave may include a terahertz wave substrate layer 911, a waveguide layer 912, a waveguide diffraction grating layer 913, a selective detection layer 914, and a filter layer 915.

In the structure illustrated in FIG. 9B, incident light diffracts and then high-order diffractive waves except for the zeroth-order can make a guided mode in the waveguide layer 912 between the substrate layer 911 and the waveguide diffraction grating layer 913. In this case, the refractive index of the waveguide layer 912 should be larger than the effective refractive index of the waveguide diffraction grating layer 913 and the refractive index of the substrate layer 911.

As another example, the waveguide layer 912 may be formed not between the substrate layer 911 and the diffraction grating layer 913, but between the diffraction grating layer 913 and the selective detection layer 914.

Referring to FIG. 9C, a wrapper for a terahertz wave may include a terahertz wave transmission layer 921, a first diffraction grating layer 922, a second diffraction grating layer 923, a selective detection layer 924, and a filter layer 925. The first diffraction grating layer 922 and the second diffraction grating layer 923 may cross each other without overlapping each other.

In the structure illustrated in FIG. 9C, the first diffraction grating layer 922 and the second diffraction grating layer 923 can diffract incident light and make a guided mode in the first diffraction grating layer 922. In this case, the average refractive index of the first diffraction grating layer 922 should be larger than the average refractive index of the second diffraction grating layer 923 and the refractive index of the terahertz wave transmission layer 921.

Other than the structure described in this embodiment, various modifications may be possible, and these structures cause an electric field enhancement effect around a waveguide layer, so sensitivity can be improved.

FIGS. 10A to 10J are views illustrating an electric field enhancement structure according to an embodiment of the present invention.

Referring to FIGS. 10A to 10J, the electric field enhancement structure may be a metamaterial. The metamaterial is an artificial material designed such that a material has negative permittivity or negative permeability, with a metal resonance structure having a size equal to or less than a wavelength as a necessary element of a lattice structure.

Referring to FIGS. 10A to 10J, a metamaterial may have various pattern shapes. The metal with a resonance structure may be generally a thin metal line or split ring resonator (SRR) as various metal patterns of FIGS. 10A to 10J, in which it is possible to freely adjust the permittivity and permeability of a material by uniformly arranging the metal resonance structures in a lattice.

In particular, when the metamaterial is formed on a uniform dielectric substrate at a terahertz band and a terahertz wave is radiated to the metamaterial, resonance is rapidly generated at a specific wavelength band, so a region where transmittance decreases is generated. In this case, the resonant frequency changes by reacting with a fine change of a selective detection layer disposed close to the metamaterial similar to the GMR and a change in material can be detected by the change in resonant frequency (see FIGS. 7A to 7C).

Similar to the GMR, the metamaterial is also known as being detected with higher sensitivity than simply radiating a terahertz wave because an electric field enhancement effect is generated close to the metamaterial, and a metamaterial will be used as an electric field enhancement structure for a wrapper by applying this principle.

Figure 11:
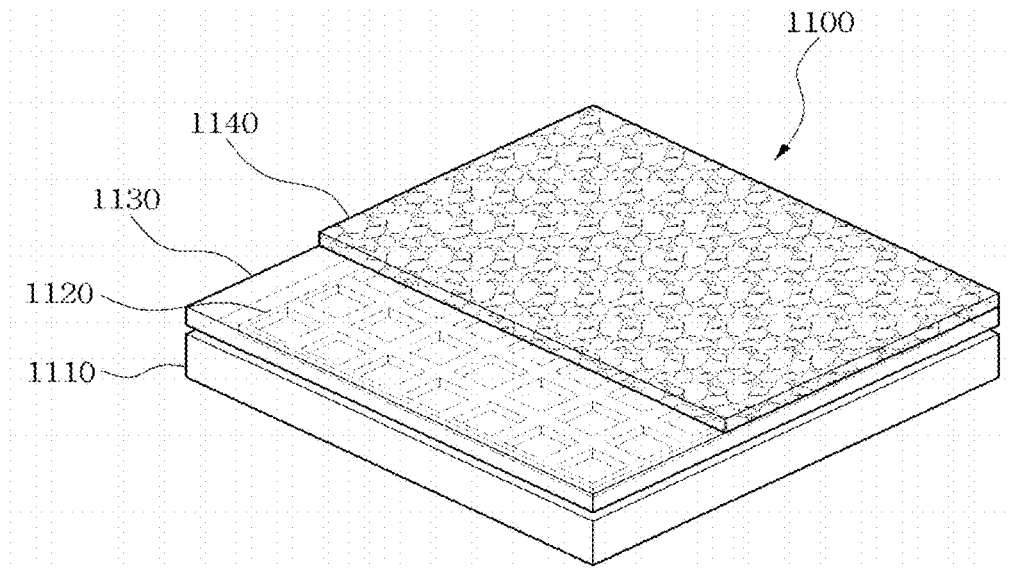
FIG. 11 is a view illustrating an electric field enhancement structure according to another embodiment of the present invention.

FIG. 11 is a view illustrating an electric field enhancement structure according to another embodiment of the present invention.

Referring to FIG. 11, a wrapper 1100 may include a substrate layer 1110, a metal net (mesh) structure 1120, a selective detection layer 1130, and a filter layer 1140. The metal net structure 1120 strongly resonate at a specific wavelength band, similar to the GMR structure, so an electric field enhancement effect can be generated close to the metal net structure. By combining the metal net structure 1120, which can generate an electric field enhancement effect in comparison to simply radiating a terahertz wave with a wrapper, a change in the wrapper can be detected with high sensitivity.

Figure 12:
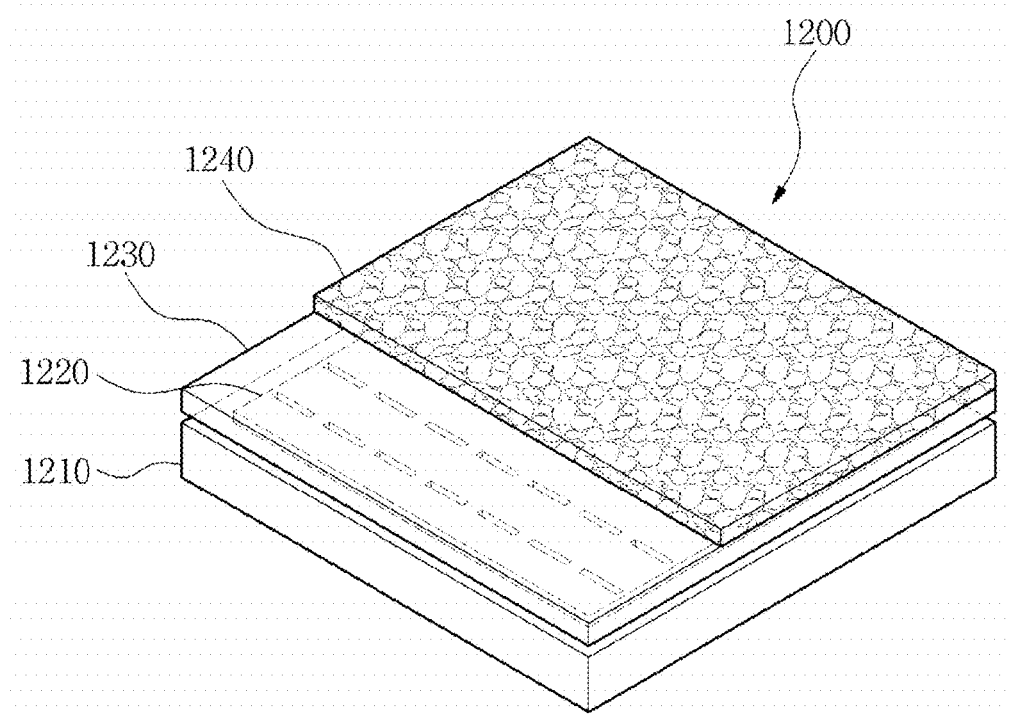
FIG. 12 is a view illustrating an electric field enhancement structure according to another embodiment of the present invention.

FIG. 12 is a view illustrating an electric field enhancement structure according to another embodiment of the present invention.

Referring to FIG. 12, a wrapper 1200 may include a substrate layer 1210, a metal layer 1220, a selective detection layer 1230, and a filter layer 1240. The metal layer 1220 includes a layer having a structure formed like a hole or a slit having a width equal to or less than the wavelength of a light source on a metal film. When a terahertz wave is radiated to the metal layer 1220, the incident terahertz wave passes through a hole or a slit at a predetermined wavelength band. While the terahertz wave passes through it, a strong electric field is formed around the hole or slit equal to or less than the resonance wavelength. Accordingly, by combining a metal layer that can generate an electric field enhancement effect in comparison to simply radiating a terahertz wave with a wrapper, a change in the wrapper can be detected with high sensitivity.

Though not illustrated in the figure, the electric field enhancement structure may be a structure that induces surface plasmon resonance at a terahertz range that can enhance an electric field close to a structure (for example, a structure based of a semiconductor or a structure based on a metamaterial) or a photonic crystal structure. Similarly, it may be used as a structure for enhancing an electric field close to a structure.

Figure 13:
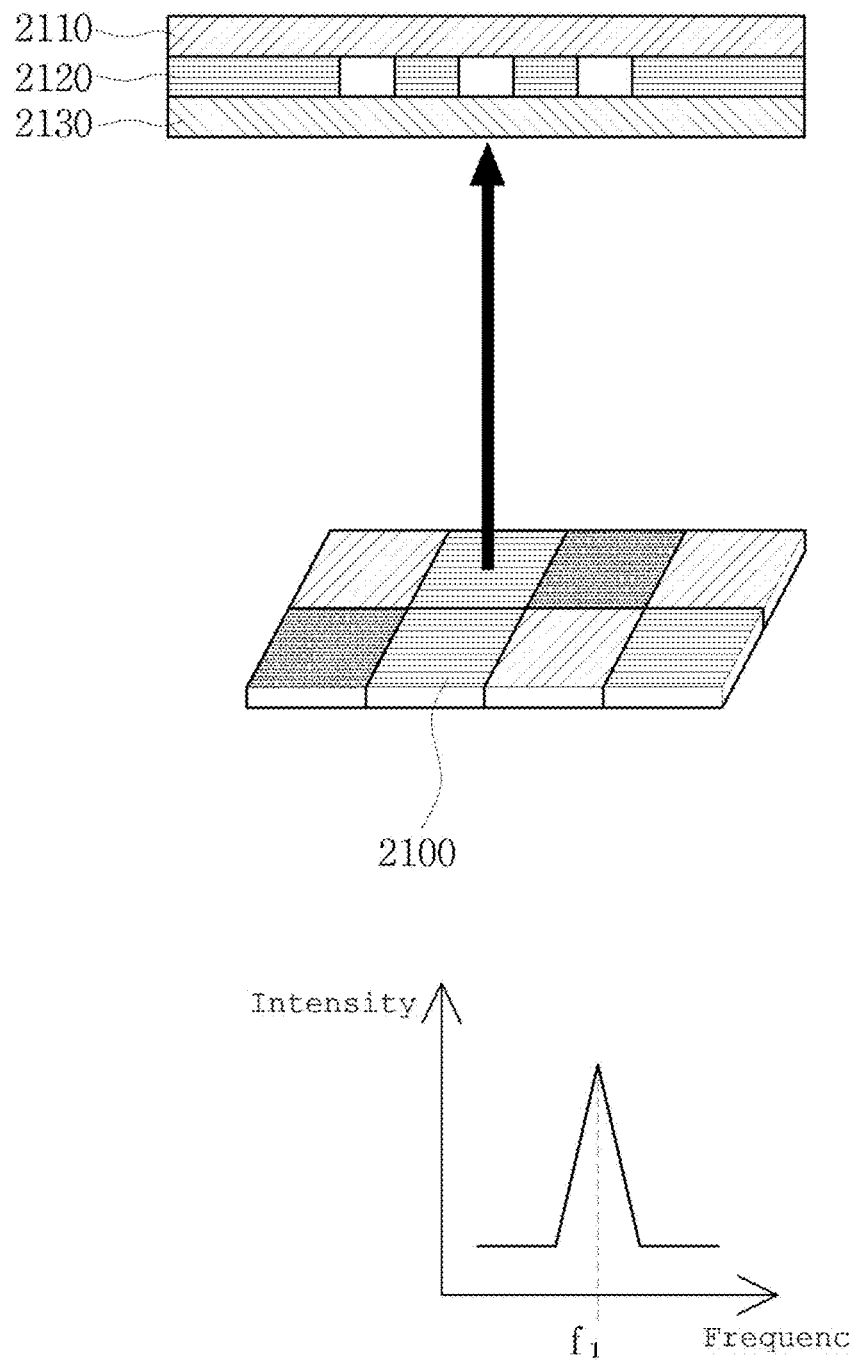
FIG. 13 is a view illustrating an optical identification device for a terahertz wave according to an embodiment of the present invention.

FIG. 13 is a view illustrating an optical identification device for a terahertz wave according to an embodiment of the present invention.

Referring to FIG. 13, an optical identification device 2100 for a terahertz wave may include m identification units. The identification units each may include a terahertz wave transmission layer 2110, a waveguide diffraction grating 2120, and a substrate layer 2130. Although a case having eight identification units is described in this embodiment, the number of the identification units is not limited thereto. The identification units can be influenced by a radiation area, a natural resonant frequency, and a grating cycle, but is most influenced by the radiation area. For example, when the radiator of a terahertz wave beam is 6 mm, the area of the identification unit may be 8 mm×8 mm. As described above, since the diameter of the terahertz wave beam is small, the area of the identification unit is also very small.

The terahertz wave transmission layer 2110 is made of a material that transmits a terahertz wave.

When a terahertz wave passing through the terahertz wave transmission layer 2110 is radiated, the waveguide diffraction grating 2120 can generate a terahertz wave having a natural resonant frequency. Herein, the natural resonant frequency may be any one of the first natural resonant frequency to the n-th natural resonant frequency. For example, the first natural resonant frequency may be f1. If n is 10, the natural resonant frequency may be any one of ten natural resonant frequencies (since the term 'natural resonant frequency' was used in patents relating to a wrapper, a resonant frequency is used herein).

The waveguide diffraction grating 2120 may be made of photosensitive, thermal-sensitive, and electric-sensitive material.

The waveguide diffraction grating 2120 may include grooves or ridges on a dielectric slab. Further, for example, the diffraction grating is a flat dielectric sheet having permittivity (for example, a phase grating) that periodically alternate in a dielectric sheet. The phase grating may be formed in a dielectric sheet by forming array of periodic holes passing through the dielectric sheet.

The waveguide diffraction grating 2120 may include any one of a one-dimensional (1D) diffraction grating and a two-dimensional diffraction grating. The 1D diffraction grating, for example, may include a set of actually straight grooves that are periodic and parallel only in a first direction (for example, x-axial direction). The 2D diffraction grating, for example, may include an array of holes in a dielectric slab or sheet, in which the holes are periodically spaced in two perpendicular directions (for example, in both of x-axial and y-axial directions). The 2D diffraction grating is also called a photonic crystal.

The substrate layer 2130 may be a layer that is combined with the waveguide diffraction grating 2120 to fix the waveguide diffraction grating 2120.

The optical identification device 2100 for a terahertz wave has an $n^m$ available identification codes when the kinds of natural resonant frequency is n and the number of identification units is m. For example, when the kind of natural resonant frequency is 10 and the number of identification units is 2, the identification code is $10^2=100$. As described above, the optical identification device 2100 for a terahertz wave can express 100 identification codes using only two identification codes. Further, for example, when the kind of natural resonant frequency is 10 and the number of identification units is 8, the identification code is $10^8=100,000,000$.

Accordingly, the optical identification device for a terahertz wave can express a large amount of identification codes in a small area.

Further, the optical identification device for a terahertz wave cannot visually recognize an optical identification device, so security is high.

FIGS. 14A to 14E are views illustrating in detail an optical identification device for a terahertz wave according to an embodiment of the present invention.

Figure 14A:
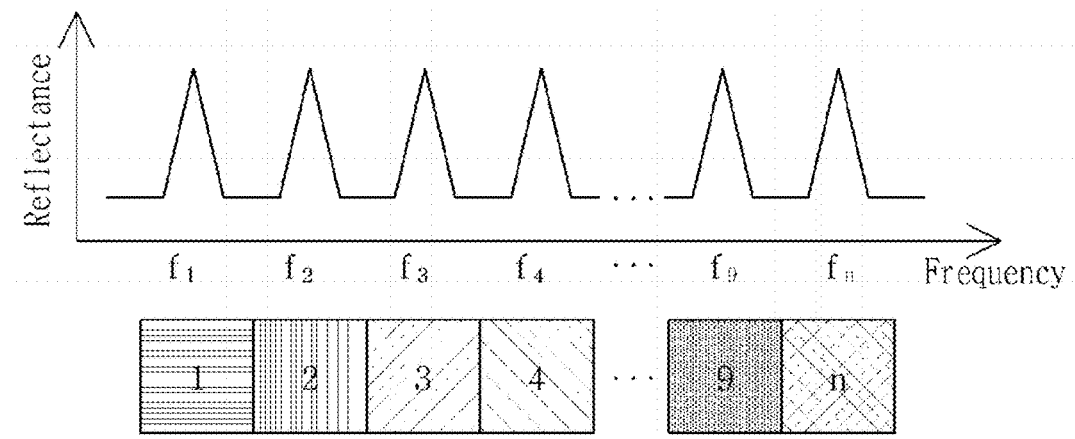

FIG. 14A is a graph illustrating a terahertz wave reflecting from an optical identification device for a terahertz wave.

Referring to FIG. 14A, identification units 1 to n may have natural resonant frequencies $f_1$, $f_2$, $f_3$, to $f_n$. For example, the first identification unit 1 may have a first natural resonant frequency $f_1$, the second identification unit 2 may have a second natural resonant frequency $f_2$, and the n-th identification unit n may have an n-th natural resonant frequency $f_n$.

Figure 14B:
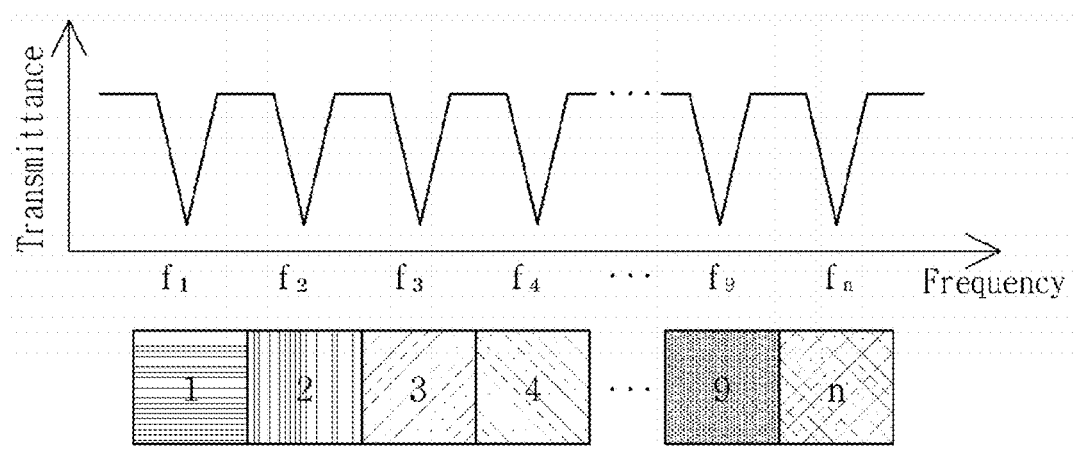

FIG. 14B is a graph illustrating a terahertz wave transmitted from an optical identification device for a terahertz wave.

Referring to FIG. 14B, identification units 1 to n may have natural resonant frequencies $f_1$, $f_2$, $f_3$, to $f_n$. For example, the first identification unit 1 may have a first natural resonant frequency $f_1$, the second identification unit 2 may have a second natural resonant frequency $f_2$, and the n-th identification unit n may have an n-th natural resonant frequency $f_n$.

FIG. 14C is a view illustrating an optical identification device for a terahertz wave composed of 16 identification units.

Referring to FIG. 14C, a total number of identification units is 16 and the sixteen identification units may be composed of ten identification units 1 to 10 having natural resonant frequencies $f_1$, $f_2$, $f_3$, to $f_{10}$. In detail, the first identification unit may be the first identification unit 1 having the first natural resonant frequency $f_1$, the second identification unit may be the fourth identification unit 4 having the fourth natural resonant frequency $f_4$, the third identification unit may be the second identification unit 2 having the second natural resonant frequency $f_2$, and the identification units at other positions may be identification units illustrated in FIG. 14C.

FIG. 14D illustrate the number of identification codes that can be expressed when the kinds of natural resonant frequency is n and the number of identification units is m.

Referring to FIG. 14D, the kinds of natural resonant frequency of identification units that can be formed in each identification unit is n and an optical identification device for a terahertz is composed of total sixteen identification units, so the available identification codes are $n^{16}$.

FIG. 14E is a view illustrating various arrangements of identification units.

Referring to FIG. 14E, the identification units can be arranged in various ways and the ways of arrangement may mean identification information different from identification codes. The identification units may be arranged in various shapes such as a line, a circle, a rectangle, a lattice, and a cross.

Referring to (a) to (c) in FIG. 14E, identification units may be arranged in a line, a cross, and a circular band. In this case, the line may mean an A article, the cross may mean a B article, and the circular band may mean a C article. As described above, the arrangement shapes of identification units may be used identification information.

FIGS. 15A to 15D are views illustrating an apparatus for recognizing an optical identification device for a terahertz wave according to an embodiment of the present invention.

Figure 15A:
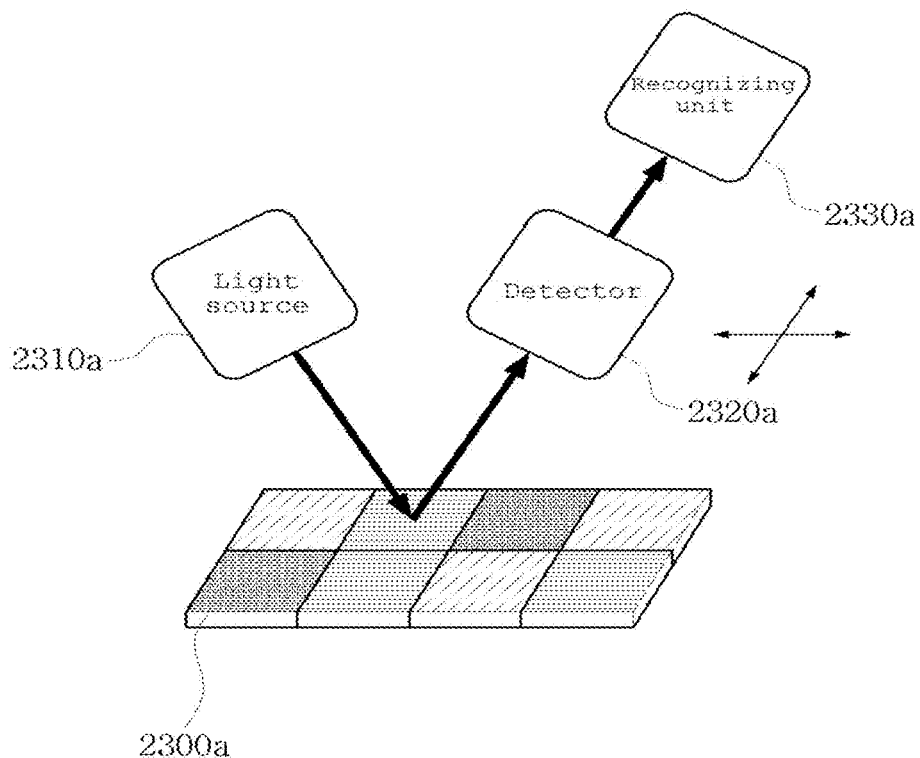
FIGS. 15A to 15D are views illustrating an apparatus for recognizing an optical identification device for a terahertz wave according to an embodiment of the present invention.

Referring to FIG. 15A, an apparatus for recognizing an optical identification device for a terahertz wave may include an optical identification device 2300a for a terahertz wave, a light source 2310a, and a detector 2320a.

The optical identification device 2300a for a terahertz wave may include a terahertz wave transmission layer made of a material that transmits a terahertz wave, and m identification units having a waveguide diffraction grating that resonates at a natural resonant frequency when receiving a transmitted terahertz wave and that is one of the first natural resonant frequency to the n-th natural resonant frequency.

The light source 2310a can radiate a terahertz wave to the optical identification device 2300a for a terahertz. For example, various devices that can generate terahertz waves may be the light source 2310a. A terahertz wave, which is an electromagnetic wave between the infrared ray and the microwave, may generally have a frequency of 0.1 THz to 10 THz. However, even if it comes a little out of this range, it may be considered as the terahertz wave stated herein if it can be easily found by those skilled in the art.

The detector 2320a can detect the natural resonant frequency of a terahertz wave reflecting from the optical identification device 2300a for a terahertz wave.

A recognition unit 2330a can recognize identification codes on the basis of the natural resonant frequency of a terahertz wave reflecting from the optical identification device 2300a for a terahertz wave. For example, when there are four identification units, the recognition unit (not illustrated) can recognize the identification codes on the basis of the kinds of the natural resonant frequencies of terahertz waves reflecting from the identification units. In detail, for example, when the natural resonant frequencies of reflecting terahertz waves are $f_1$, $f_9$, $f_2$, $f_3$, identification codes may be 1/9/2/3. As described above, the digits of identification codes are expressed not simply by 0/1, but may be expressed by numbers the same as natural resonant frequencies. When the kinds of natural resonant frequencies are 15, the digits of identification codes can be expressed by 0 to 15, so the number of available identification codes $15^4$.

A light source-detector moving unit (not illustrated) can move a light source 2310a such that a terahertz wave generated from the light source 2310a is sequentially radiated to the identification units, and can move the detector 2320a as much as the movement of the light source 2310a. Accordingly, the apparatus for recognizing an optical identification device for a terahertz wave can scan the identification units by moving the light source 2310a and the detector 2320a, with the optical identification device 2300a for a terahertz wave fixed.

Figure 15B:
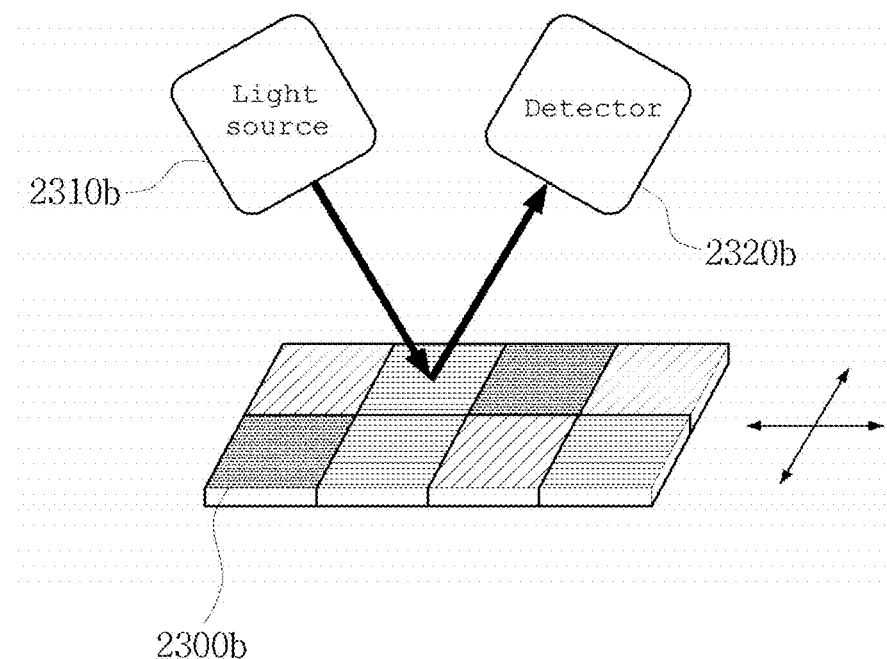

Referring to FIG. 15B, an apparatus for recognizing an optical identification device for a terahertz wave may include an optical identification device 2300b for a terahertz wave, a light source 2310b, and a detector 2320b.

The optical identification device 2300b for a terahertz wave may include a terahertz wave transmission layer made of a material that transmits a terahertz wave, and m identification units that resonates at a natural resonant frequency when receiving a transmitted terahertz wave, and have a waveguide diffraction grating having a natural resonant frequency that is any one of the first natural resonant frequency to the n-th natural resonant frequency.

The light source 2310b can radiate a terahertz wave to the optical identification device 2300b for a terahertz wave.

The detector 2320b can detect the natural resonant frequency of a terahertz wave reflecting from the optical identification device 2300b for a terahertz wave.

An optical identification device moving unit (not illustrated) can move the optical identification device 2300b for a terahertz wave such that a terahertz wave generated from the light source 2310b is sequentially radiated to the identification units. Accordingly, the apparatus for recognizing an optical identification device for a terahertz wave can scan the identification units by moving the optical identification device 2300a for a terahertz, with the light source 2310a and the detector 2320a fixed.

Figure 15C:
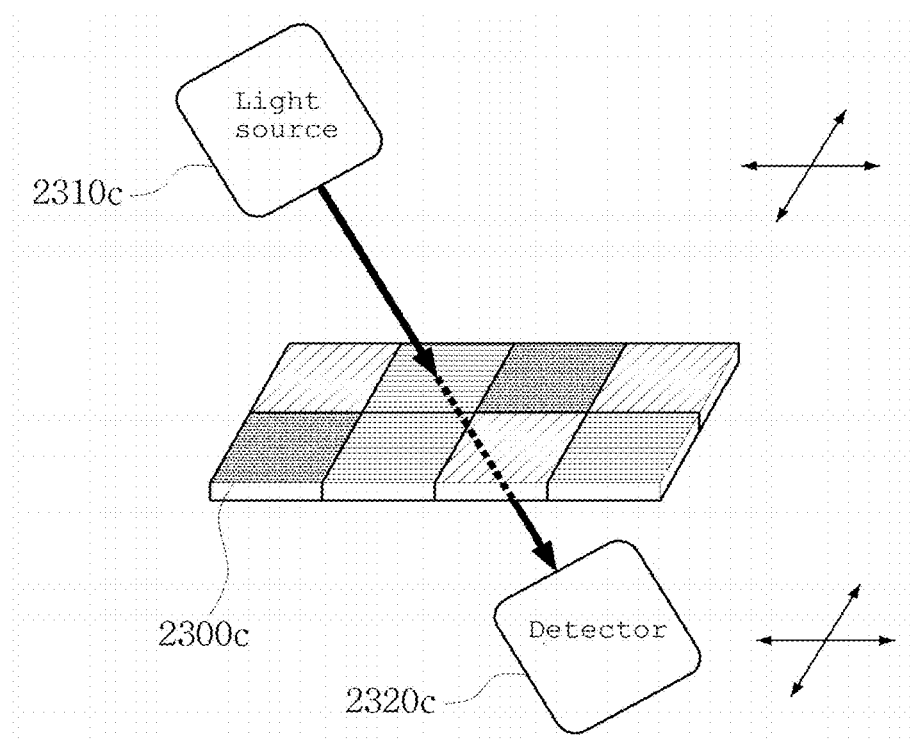

Referring to FIG. 15C, an apparatus for recognizing an optical identification device for a terahertz wave may include an optical identification device 2300c for a terahertz wave, a light source 2310c, and a detector 2320c.

The optical identification device 2300c for a terahertz wave may include a terahertz wave transmission layer made of a material that transmits a terahertz wave, and m identification units that resonates at a natural resonant frequency when receiving a transmitted terahertz wave, and have a waveguide diffraction grating having a natural resonant frequency that is any one of the first natural resonant frequency to the n-th natural resonant frequency.

The light source 2310c can radiate a terahertz wave to the optical identification device 2300c for a terahertz wave.

The detector 2320c can detect the natural resonant frequency of a terahertz wave transmitted from the optical identification device 2300c for a terahertz wave.

A light source-detector moving unit (not illustrated) can move a light source 2310c such that a terahertz wave generated from the light source 2310c is sequentially radiated to the identification units, and can move the detector 2320c as much as the movement of the light source 2310c. Accordingly, the apparatus for recognizing an optical identification device for a terahertz wave can scan the identification units by moving the light source 2310c and the detector 2320c, with the optical identification device 2300c for a terahertz fixed.

Figure 15D:
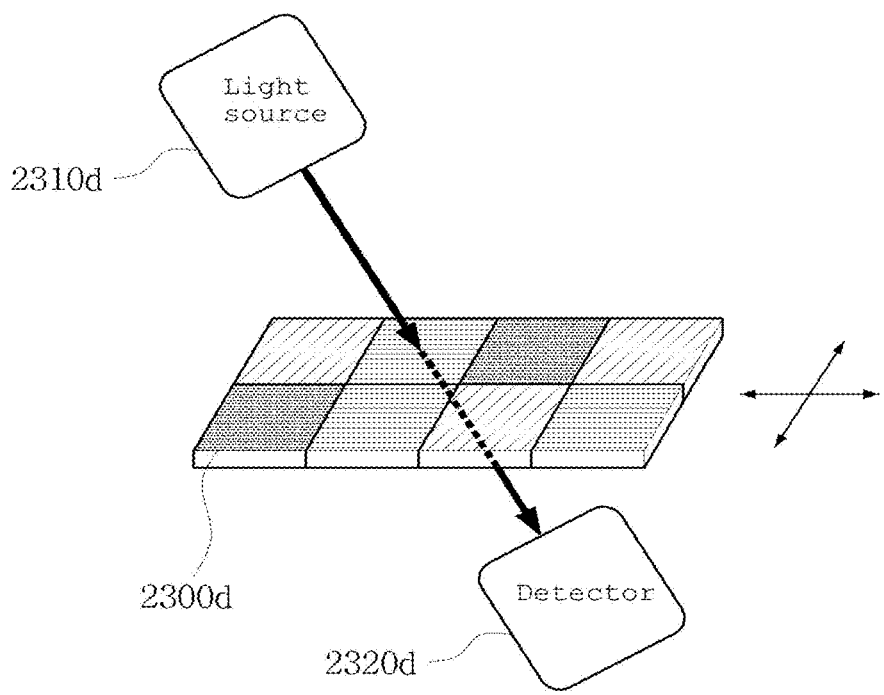

Referring to FIG. 15D, an apparatus for recognizing an optical identification device for a terahertz wave may include an optical identification device 2300d for a terahertz wave, a light source 2310d, and a detector 2320d.

The optical identification device 2300*d* for a terahertz wave may include a terahertz wave transmission layer made of a material that transmits a terahertz wave, and m identification units that resonates at a natural resonant frequency when receiving a transmitted terahertz wave, and having a waveguide diffraction grating having a natural resonant frequency that is any one of the first natural resonant frequency to the n-th natural resonant frequency.

The light source 2310*d* can radiate a terahertz wave to the optical identification device 2300*d* for a terahertz wave.

The detector 2320*d* can detect the natural resonant frequency of a terahertz wave transmitted from the optical identification device 2300*d* for a terahertz wave.

An optical identification device moving unit (not illustrated) can move the optical identification device 2300*d* for a terahertz wave such that a terahertz wave generated from the light source 2310*d* is sequentially radiated to the identification units. Accordingly, the apparatus for recognizing an optical identification device for a terahertz wave can scan the identification units by moving the optical identification device 2300*d* for a terahertz, with the light source 2310*d* and the detector 2320*d* fixed.

Figure 16:
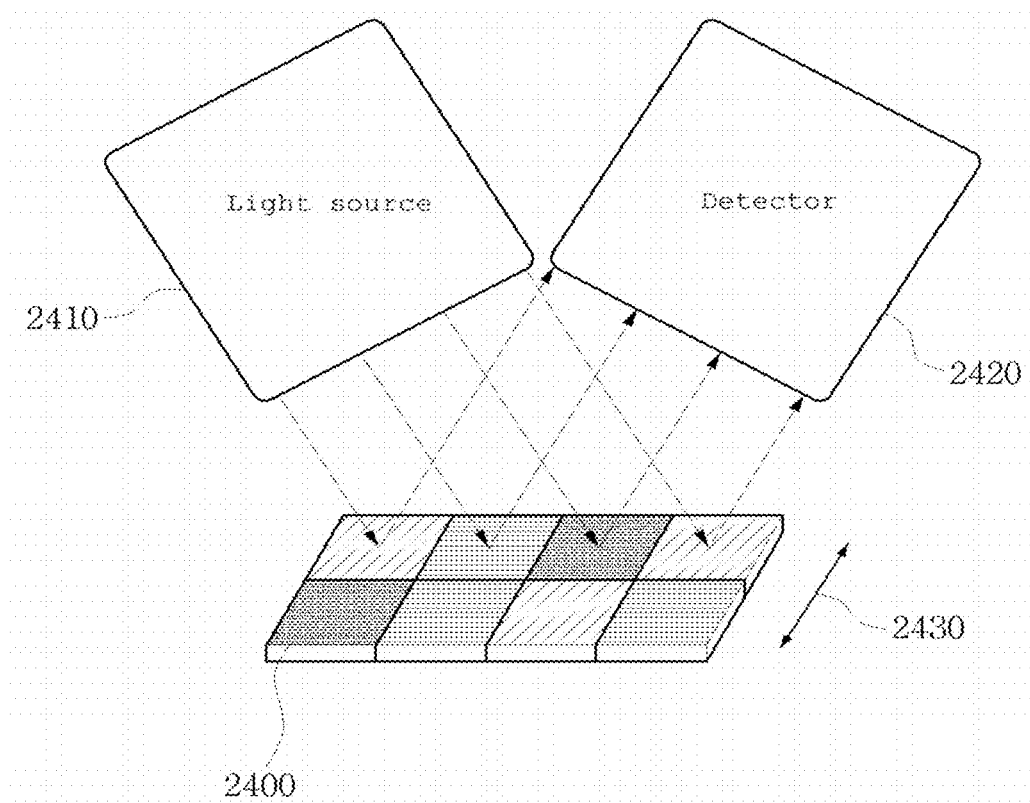
FIG. 16 is a view illustrating an apparatus for recognizing an optical identification device for a terahertz wave according to another embodiment of the present invention.

FIG. 16 is a view illustrating an apparatus for recognizing an optical identification device for a terahertz wave according to another embodiment of the present invention.

Referring to FIG. 16, an apparatus for recognizing an optical identification device for a terahertz wave may include an optical identification device 2400 for a terahertz wave, a light source 2410, and a detector 2420.

The light source 2410 may be an array including a plurality of light sources that can generate terahertz waves.

The detector 2420 may be a detector array including a plurality of detectors and matched with the light source array.

In this embodiment, the light source 2410 may be an array with four light sources arranged in a line and the detector 2420 may be an array with four detectors arranged in a line. The detector 2420 array can be matched with the light source array one to one.

An optical identification device moving unit (not illustrated) can move (2430) the optical identification device 2400 for a terahertz wave such that a terahertz wave generated from the light source array is sequentially radiated to the identification units. Accordingly, the apparatus for recognizing an optical identification device for a terahertz wave can scan the identification units by moving the optical identification device 2400 for a terahertz, with the light source array and the detector array fixed.

Figure 17:
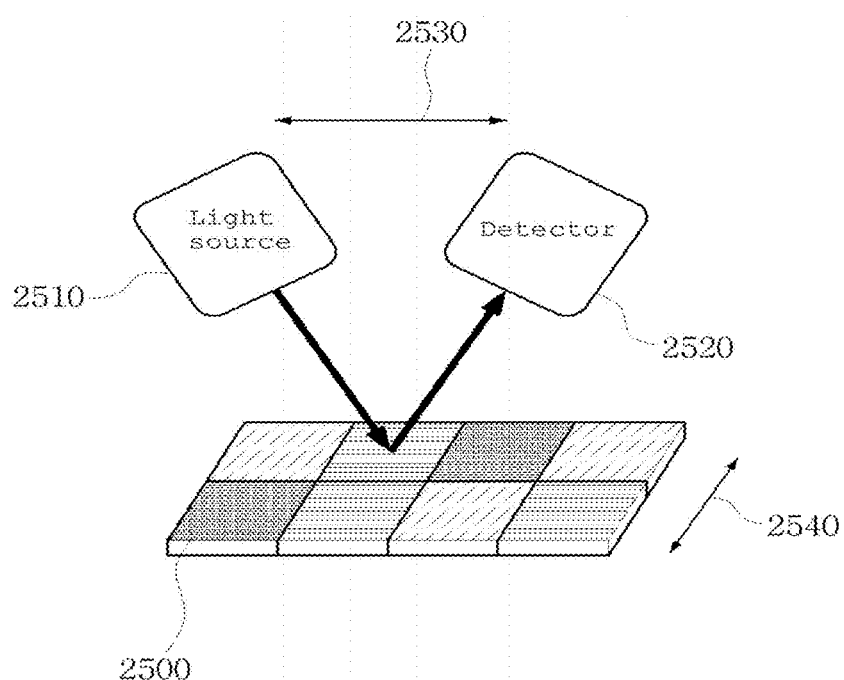
FIG. 17 is a view illustrating an apparatus for recognizing an optical identification device for a terahertz wave according to another embodiment of the present invention.

FIG. 17 is a view illustrating an apparatus for recognizing an optical identification device for a terahertz wave according to another embodiment of the present invention.

Referring to FIG. 17, an apparatus for recognizing an optical identification device for a terahertz wave may include an optical identification device 2500 for a terahertz wave, a light source 2510, and a detector 2520.

The light source 2510 can radiate a terahertz wave to the optical identification device 2500 for a terahertz wave.

The detector 2520 can detect the natural resonant frequency of a terahertz wave transmitted from the optical identification device 2500 for a terahertz wave.

A light source-detector moving unit (not illustrated) can move the light source 2510 in one direction 2530 and move the detector 2520 as much as the movement of the light source 2510.

An optical identification device moving unit (not illustrated) can move the optical identification device 2500 for a terahertz wave in another direction 2540.

Accordingly, an apparatus for recognizing an optical identification device for a terahertz wave can scan the identification units by organically moving the optical identification device 2500 for a terahertz wave, the light source 2510, and the detector 2520.

Figure 18A:
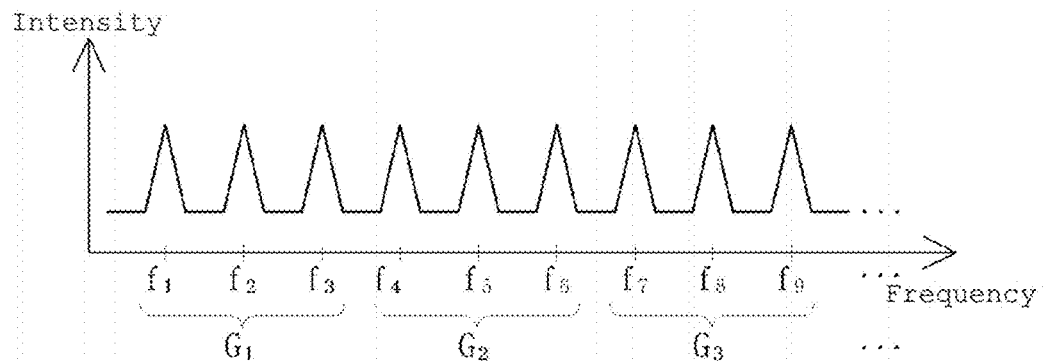
FIGS. 18A to 18C are views illustrating a writing apparatus for an identification unit according to an embodiment of the present invention.
Figure 18B:
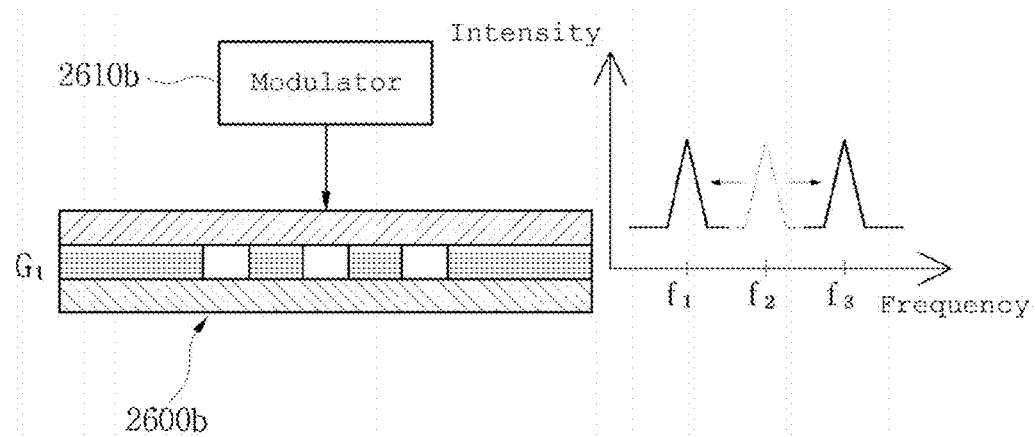
Figure 18C:
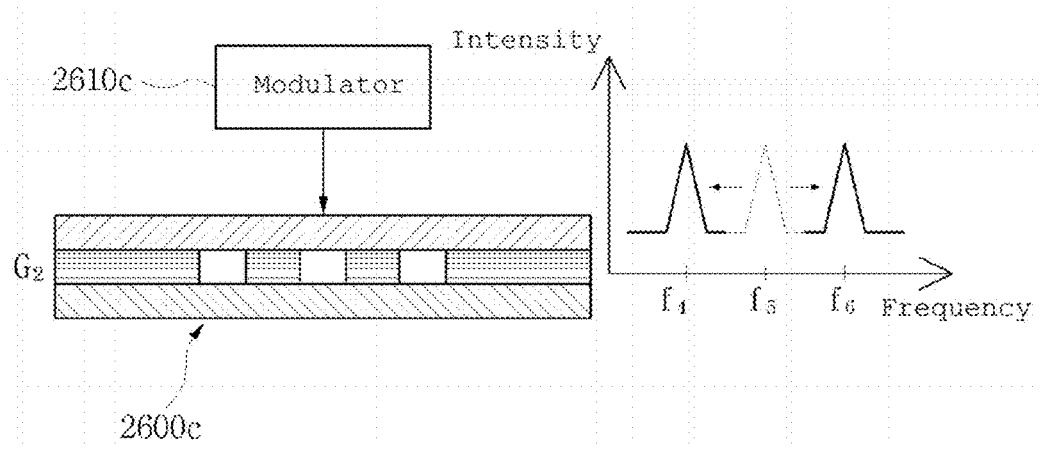

FIGS. 18A to 18C are views illustrating a writing apparatus for an identification unit according to an embodiment of the present invention.

Referring to FIG. 18A, a natural resonant frequency can be set for each of frequency bands G1, G2, to Gm. The frequency bands can be set on the basis of frequency bands that can be changed by a modulator 2610*b* (FIG. 18B). For example, when the frequency band that can be changed by the modulator 2610*b* (FIG. 18B) with respect to $f_2$ is $f_1$ to $f_3$, the first frequency band G1 is $f_1$ to $f_3$. When the frequency band that can be changed by the modulator 2610*b* (FIG. 18B) with respect to $f_5$ is $f_4$ to $f_6$, the first frequency band G1 is $f_4$ to $f_6$.

Referring to FIG. 18B, a writing apparatus for an identification unit may include an identification unit 2600*b* and a modulator 2610*b*. The identification unit 2600*b* may include a terahertz wave transmission layer made of a material that can transmit terahertz wave and a waveguide diffraction grating having a natural resonant frequency corresponding to a frequency band G1 for a transmitted terahertz wave.

The modulator 2610*b* can change the natural resonant frequency of the waveguide diffraction grating to another natural resonant frequency in a predetermined frequency band. For example, the modulator 2610*b* can change the natural resonant frequency $f_2$ of the waveguide diffraction grating to another natural resonant frequency $f_1$ or $f_3$ in a predetermined waveguide band G1.

As a detailed method of changing a resonant frequency, for example, the modulator 2610 can change the natural resonant frequency of the waveguide diffraction grating to another natural resonant frequency in a predetermined frequency band. This will be described below with respect to FIG. 19.

Referring to FIG. 18C, a writing apparatus for an identification unit may include an identification unit 2600*c* and a modulator 2610*c*. The identification unit 2600*c* may include a terahertz wave transmission layer made of a material that can transmit terahertz wave and a waveguide diffraction grating having a natural resonant frequency $f_5$ corresponding to a frequency band G2 for a transmitted terahertz wave.

The modulator 2610*c* can change the natural resonant frequency of the waveguide diffraction grating to another natural resonant frequency in a predetermined frequency band. The modulator 2610*c* can change the natural resonant frequency $f_5$ of the waveguide diffraction grating to another natural resonant frequency $f_4$ or $f_6$ in a predetermined waveguide band G2.

As described above, by using the writing apparatus for an identification unit, a user can freely change the resonant frequency of an identification unit within a predetermined resonant frequency range. Accordingly, there is no need for manufacture an identification unit for each resonant frequency, so it is possible to reduce the manufacturing cost of an identification unit and an optical identification device. Further, since a user, and the like changes an identification unit to a desired resonant frequency at the site using the writing apparatus for an identification unit, convenience for the user can be improved.

Figure 19A:
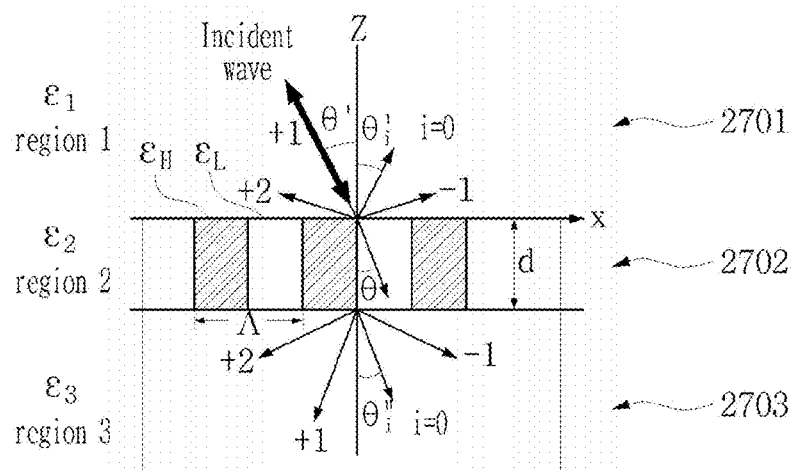
FIGS. 19A to 19C are views illustrating a waveguide diffraction grating according to an embodiment of the present invention.
Figure 19B:
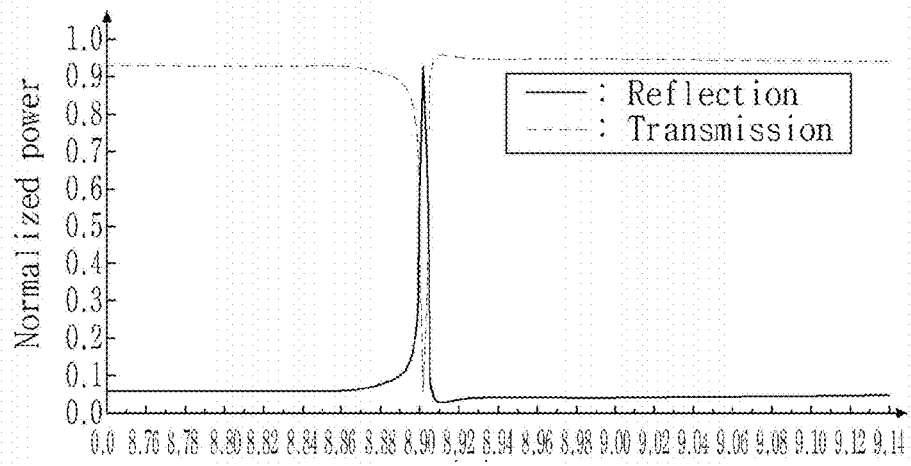
Figure 19C:
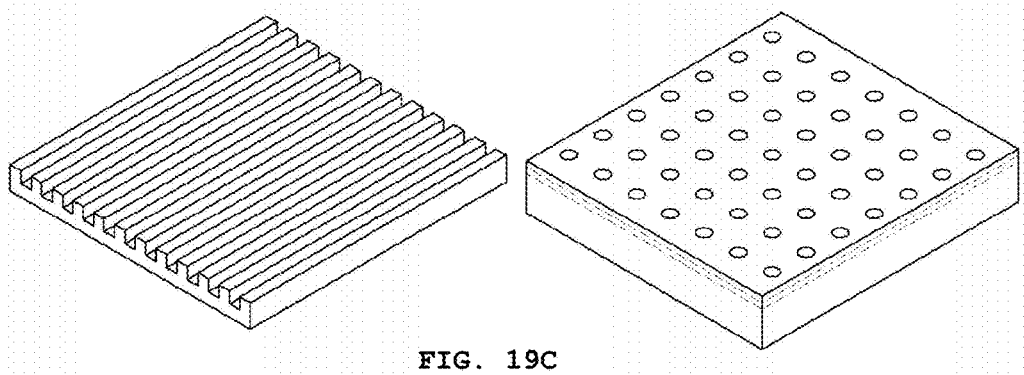

FIGS. 19A to 19C are views illustrating a waveguide diffraction grating according to an embodiment of the present invention.

Referring to FIG. 19A, an identification unit may include a waveguide diffraction grating that causes GMR (Guided mode Resonance) at a specific frequency.

The waveguide diffraction grating layer 2702 can diffract incident light under given conditions (the frequency of incident light, an incident angle, and the thickness and effective refractive index of a waveguide). Except for the zeroth order, high-order diffractive waves can generate a guided mode in the waveguide diffraction grating layer 2702. In this case, a zeroth-order reflected wave-transmitted wave make phase matching with the guided mode and the energy of the guided mode generates resonance transmitted back to the zeroth-order reflected wave-transmitted wave. With the resonance, a zeroth-order reflected-diffracted wave is 100% reflected due to constructive interference and the zeroth-order transmitted-diffracted wave is 0% transmitted by offset interference, so a very sharp resonance curve is constructed at a specific frequency band.

FIG. 19B illustrates a GMR result in which a diffraction grating ($n_H$=1.80, $n_L$=1.72, thickness=80 um, cycle=200 um) is made of SU-8 photoresist on a transparent polymethylpentene substrate (n=1.46) at a terahertz band and is calculated by FDM (resonance is generated at 0.89 THz).

As illustrated in FIG. 19A, assuming that the permittivity of a cover layer 2701 is $\varepsilon_1$, the permittivity of a waveguide diffraction grating layer 2702 is $\varepsilon_2$, and the permittivity of a substrate layer 2703 is $\varepsilon_3$, the permittivity $\varepsilon_2$ of a waveguide diffraction grating layer can be expressed as in the following equation 1.

$$\varepsilon_2(X)=\varepsilon_g+\Delta\varepsilon^*\cos(Kx) \qquad [\text{Equation 1}]$$

where $\varepsilon_g$ is the average of two permittivities ($\varepsilon_H$, $\varepsilon_L$) constituting a diffraction grating and repeated, $\Delta\varepsilon$ is the maximum change of permittivity, K is spatial the frequency of a grating, $2\pi/\Lambda$, $\Lambda$ is a period of a grating, and x is the distance from the origin in the X-axial direction.

In this case, the effective permittivity N of a waveguide has only to satisfy the following condition so that a waveguide diffraction grating resonates at a specific frequency and incident angle of incident light, that is, a waveguide mode is generated.

$$\max(\sqrt{\varepsilon_1},\sqrt{\varepsilon_2})|N|<\sqrt{\varepsilon_g}$$

In particular, it is possible to induce the refractive index change $\Delta\varepsilon$ by applying appropriate light, heat, or electricity to the diffraction grating, by injecting a photochromic material, a thermochromic material, or an electrochromic material into the waveguide diffraction grating. For example, it is possible to change the resonant frequency of the waveguide diffraction grating by changing $\Delta\varepsilon$ by applying light, heat, or electricity through the modulator 2610b.

FIG. 19C is a perspective view illustrating the structure and shape of a waveguide diffraction grating.

The diffraction grating may include grooves or ridges on a dielectric slab. Further, for example, the diffraction grating is a flat dielectric sheet having permittivity (for example, a phase grating) that periodically alternate in a dielectric sheet. The phase grating may be formed in a dielectric sheet by forming array of periodic holes passing through the dielectric sheet.

As another example, the diffraction grating may include any one of a one-dimensional (1D) diffraction grating and a two-dimensional diffraction grating. The 1D diffraction grating, for example, may include a set of actually straight grooves that are periodic and parallel only in a first direction (for example, x-axial direction). The 2D diffraction grating, for example, may include an array of holes in a dielectric slab or sheet, in which the holes are periodically spaced in two perpendicular directions (for example, in both of x-axial and y-axial directions). The 2D grating is also called a photonic crystal.

FIGS. 20A to 20J are views illustrating examples when an optical identification device for a terahertz wave according to an embodiment of the present invention is applied to objects.

An optical identification device 2800 for a terahertz wave illustrated in FIGS. 20A to 20J is visually illustrated for description, but actually, a person cannot visually find the optical identification device 2800 for a terahertz wave.

Figure 20A:
FIGS. 20A to 20J are views illustrating examples when an optical identification device for a terahertz wave according to an embodiment of the present invention is applied to objects.

Referring to FIG. 20A, the optical identification device 2800 for a terahertz wave can be attached to or inserted in a military hat or uniform, and the like. In this case, the optical identification device 2800 for a terahertz wave may be used as a mark for distinguishing our force and an enemy force.

Figure 20B:
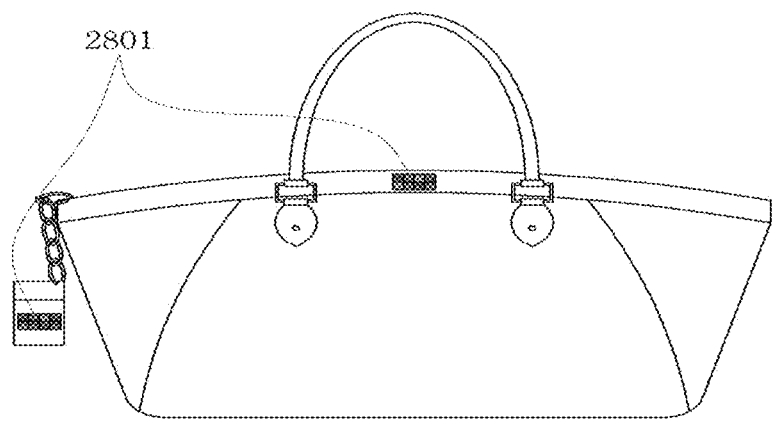

Referring to FIG. 20B, the optical identification device 2801 for a terahertz wave can be attached to or inserted in a ring or an inside skin of an expensive bag, and the like. In this case, the optical identification device 2801 for a terahertz wave may be used as a mark for distinguishing a genuine article and an imitation.

Figure 20C:
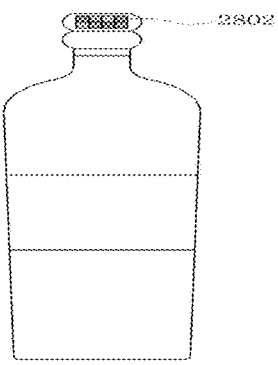

Referring to FIG. 20C, the optical identification device 2802 for a terahertz wave can be attached to or inserted in a bottle keeping expensive alcohol, and the like. In this case, the optical identification device 2802 for a terahertz wave may be used as a mark for distinguishing a genuine article and an imitation.

Figure 20D:
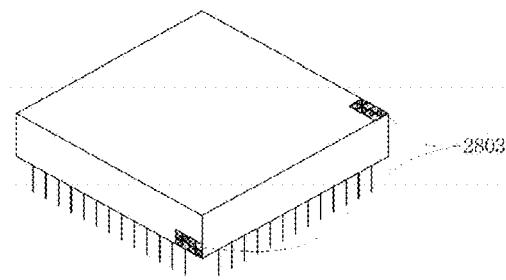

Referring to FIG. 20D, the optical identification device 2803 for a terahertz wave can be attached to or inserted in an IC chip, and the like. In this case, the optical identification device 2803 for a terahertz wave may be used as a mark for identifying a plurality of IC chips.

Figure 20E:
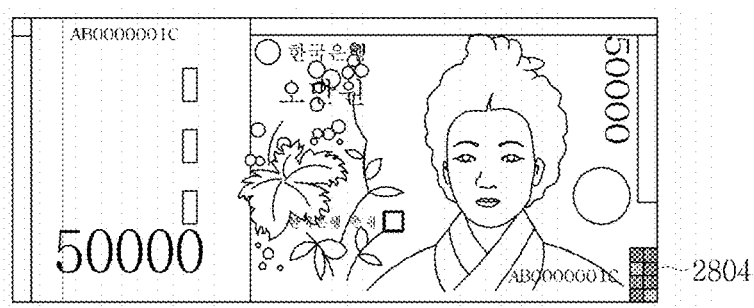

Referring to FIG. 20E, the optical identification device 2804 for a terahertz wave can be attached to or inserted in money, and the like. In this case, the optical identification device 2804 for a terahertz wave may be used as a mark for distinguishing genuine money and counterfeit money.

Figure 20F:
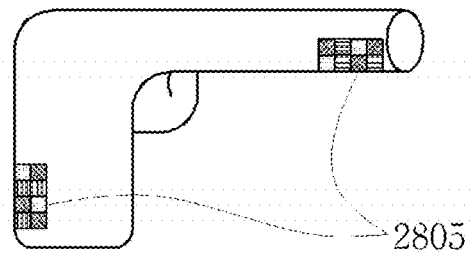

Referring to FIG. 20F, the optical identification device 2805 for a terahertz wave can be attached to or inserted in firearms, and the like. In this case, the optical identification device 2805 for a terahertz wave may be used as a mark for identifying a plurality of firearms.

Figure 20G:
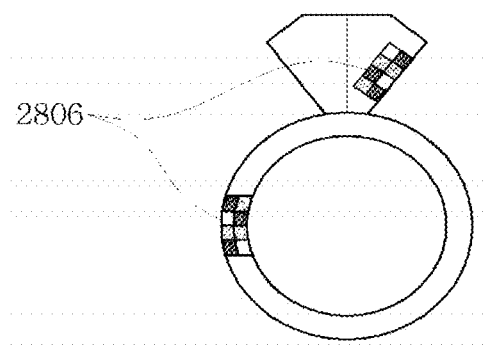

Referring to FIG. 20G, the optical identification device 2806 for a terahertz wave can be attached to or inserted in expensive accessories, and the like. In this case, the optical identification device 2806 for a terahertz wave may be used as a mark for distinguishing a genuine article and an imitation.

Figure 20H:
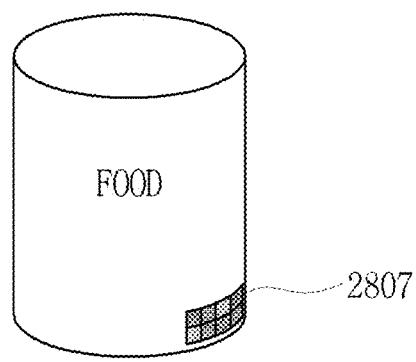

Referring to FIG. 20H, the optical identification device 2807 for a terahertz wave can be attached to or inserted in food containers, and the like. In this case, the optical identification device 2807 for a terahertz wave may be used as a mark for identifying a plurality of food containers.

Figure 20I:
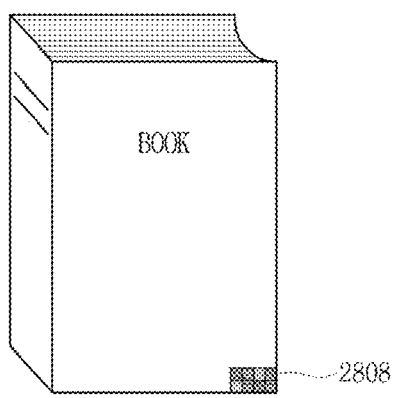

Referring to FIG. 20I, the optical identification device 2808 for a terahertz wave can be attached to or inserted in books, and the like. In this case, the optical identification device 2808 for a terahertz wave may be used as a mark for identifying a plurality of books.

Figure 20J:
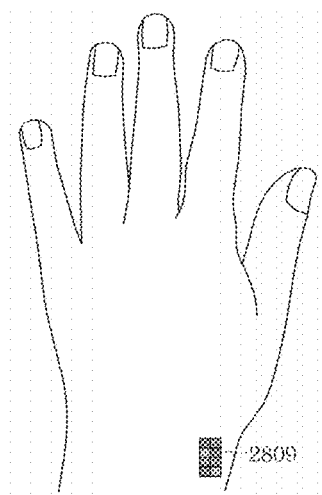

Referring to FIG. 20J, the optical identification device 2809 for a terahertz wave can be attached to or inserted in a human body or an animal. In this case, the optical identification device 2809 for a terahertz wave may be used as a mark for identifying a human body or an animal.

The optical identification device for a terahertz wave according to this embodiment can be attached to or inserted in various articles other than the examples described above.

The embodiments may be selectively partially or fully combined for various modifications.

Further, the embodiments are provided to not limit, but describe the present invention. Further, it will be apparent to those skilled in the art that various changes and modifications may be made without departing from the spirit and scope of the invention.

The invention claimed is:

1. An optical identification device for a terahertz wave, comprising:
a plurality of identification units disposed in a non-array group form,
wherein the plurality of identification units are arranged adjacent to each other in such a way that each identification unit has a different natural resonant frequency from adjacent identification units, thereby enabling expression of a large number of identification codes in a small area of the optical identification device, the optical identification device for the terahertz wave having $n^m$ available identification codes,
wherein n is a number of kinds of natural resonant frequencies and m is a number of the identification units; and
wherein each identification unit includes:
a substrate,
a waveguide diffraction grating disposed on the substrate, and
a terahertz wave transmission layer disposed on the waveguide diffraction grating, the terahertz wave transmission layer comprising a material configured to transmit a terahertz wave, wherein the waveguide diffraction grating causes guided mode resonance (GMR) at a natural resonant frequency and resonates at the natural resonant frequency when the transmitted terahertz wave is radiated, in which the natural resonant frequency is any one of a first natural resonant frequency to an n-th natural resonant frequency.

2. The optical identification device of claim 1, wherein an arrangement of the identification units means identification information different from an identification code.

3. The optical identification device of claim 2, wherein the identification units are arranged in a shape of at least any one of a line, a circle, a rectangle, a lattice, or a cross.

4. The optical identification device of claim 1, wherein the waveguide diffraction grating includes grooves or ridges on a dielectric slab.

5. The optical identification device of claim 1, wherein the waveguide diffraction grating includes a flat dielectric sheet having permittivity that periodically alternate in a dielectric sheet.

6. The optical identification device of claim 1, wherein the waveguide diffraction grating includes a dielectric sheet comprising an array of holes passing through the dielectric sheet.

7. The optical identification device of claim 1, wherein the waveguide diffraction grating includes a one-dimensional diffraction grating or a two-dimensional diffraction grating.

8. An apparatus for recognizing an optical identification device for a terahertz wave, the apparatus comprising:
an optical identification device for a terahertz wave including a plurality of identification units, each of the identification units including a substrate, a waveguide diffraction grating disposed on the substrate, and a terahertz wave transmission layer disposed on the waveguide grating and comprising a material transmitting a terahertz wave, wherein the identification units are disposed in a non-array group form and are arranged adjacent to each other in such a way that each identification unit has a different natural resonant frequency from adjacent identification units, thereby enabling expression of a large number of identification codes in a small area of the optical identification device, the optical identification device for the terahertz wave having $n^m$ available identification codes, wherein n is a number of kinds of natural resonant frequencies and m is a number of the identification units; and wherein the waveguide diffraction grating is configured to cause guided mode resonance (GMR) at a natural resonant frequency and resonate at the natural resonant frequency when the transmitted terahertz wave is radiated, in which the natural resonant frequency is any one of a first natural resonant frequency to an n-th natural resonant frequency;
a light source configured to radiate the terahertz wave to the optical identification device; and
a detector configured to detect the natural resonant frequency of the terahertz wave generated from the optical identification device.

9. The apparatus of claim 8, further comprising a recognizing unit configured to recognize identification codes based on natural resonant frequencies detected for the identification units, respectively.

10. The apparatus of claim 8, further comprising a light source-detector moving unit configured to move the light source such that a terahertz wave generated from the light source is radiated sequentially to the identification units, and moving the detector as much as a movement of the light source.

11. The apparatus of claim 8, further comprising an optical identification device moving unit configured to move the optical identification device for a terahertz wave such that a terahertz wave generated from the light source is radiated sequentially to the identification units.

12. The apparatus of claim 8, further comprising:
a light source-detector moving unit configured to move the light source in one direction and move the detector as much as the movement of the light source; and
an optical identification device moving unit configured to move the optical identification device for a terahertz wave in another direction.

13. The apparatus of claim 8, wherein the light source comprises a light source array including several light sources capable of generating a terahertz wave, and the detector comprises a detector array including several detectors matched with the light source array.

* * * * *